US008764532B1

(12) United States Patent
Berme

(10) Patent No.: US 8,764,532 B1
(45) Date of Patent: Jul. 1, 2014

(54) SYSTEM AND METHOD FOR FALL AND/OR CONCUSSION PREDICTION

(71) Applicant: Bertec Corporation, Columbus, OH (US)

(72) Inventor: Necip Berme, Worthington, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 13/853,917

(22) Filed: Mar. 29, 2013

Related U.S. Application Data

(60) Provisional application No. 61/723,703, filed on Nov. 7, 2012.

(51) Int. Cl.
*G07F 17/32* (2006.01)

(52) U.S. Cl.
USPC ............. 463/7; 463/36; 463/46; 434/258; 600/595

(58) Field of Classification Search
USPC .......................... 434/258; 463/7, 36
See application file for complete search history.

(56) References Cited

U.S. PATENT DOCUMENTS

| | | | |
|---|---|---|---|
| 5,846,134 A | 12/1998 | Latypov | |
| 6,038,488 A | 3/2000 | Barnes et al. | |
| 6,063,046 A * | 5/2000 | Allum | 600/595 |
| 6,113,237 A | 9/2000 | Ober et al. | |
| 6,152,564 A | 11/2000 | Ober et al. | |
| 6,295,878 B1 | 10/2001 | Berme | |
| 6,354,155 B1 | 3/2002 | Berme | |
| 6,389,883 B1 | 5/2002 | Berme et al. | |
| 6,738,065 B1 | 5/2004 | Even-Zohar | |
| 6,774,885 B1 | 8/2004 | Even-Zohar | |
| 6,936,016 B2 | 8/2005 | Berme et al. | |
| 7,931,604 B2 | 4/2011 | Even-Zohar et al. | |
| 7,980,856 B2 * | 7/2011 | Grabiner et al. | 434/258 |
| 8,181,541 B2 | 5/2012 | Berme | |
| 8,315,822 B2 | 11/2012 | Berme et al. | |
| 8,315,823 B2 | 11/2012 | Berme et al. | |
| 2003/0216656 A1 | 11/2003 | Berme et al. | |

(Continued)

OTHER PUBLICATIONS

U.S. Appl. No. 13/348,506, entitled "Force Measurement System Having a Plurality of Measurement Surfaces", Inventor: Dr. Necip Berme, filed Jan. 11, 2012.

(Continued)

*Primary Examiner* — Omkar Deodhar
(74) *Attorney, Agent, or Firm* — The Law Office of Patrick F. O'Reilly, III, LLC

(57) ABSTRACT

A fall and/or concussion prediction system includes: (i) a measurement assembly configured to receive a subject having a surface for receiving at least one portion of a body of a subject and at least one measurement device, the at least one measurement device configured to sense one or more measured quantities and output one or more signals that are generated based upon the subject's contact with the surface; (ii) a visual display device, the visual display device configured to display a task, an interactive game, a virtual reality scenario, and/or an immersive graphic environment that is visible to the subject; and (iii) a data processing device operatively coupled to the at least one measurement device of the measurement assembly and the visual display device. In one embodiment, a dual-task protocol is used to assess a person's risk for falling and/or predict whether or not a person has sustained a concussion.

24 Claims, 21 Drawing Sheets

(56) References Cited

U.S. PATENT DOCUMENTS

| | | |
|---|---|---|
| 2008/0221487 A1 | 9/2008 | Zohar et al. |
| 2008/0228110 A1 | 9/2008 | Berme |
| 2009/0059096 A1 | 3/2009 | Yamamoto et al. |
| 2010/0131113 A1 | 5/2010 | Even-Zohar |
| 2011/0277562 A1 | 11/2011 | Berme |
| 2012/0266648 A1 | 10/2012 | Berme et al. |
| 2012/0271565 A1 | 10/2012 | Berme et al. |
| 2013/0117377 A1 | 5/2013 | Miller |

OTHER PUBLICATIONS

BalanceCheck Screener—Protocol Guide, Bertec Corporation, Version 1.1.0, last updated Mar. 2012.

BalanceCheck Trainer—Protocol Guide, Bertec Corporation, Version 1.1.0, last updated Mar. 2012.

* cited by examiner

SYSTEM AND METHOD FOR FALL AND/OR CONCUSSION PREDICTION

CROSS-REFERENCE TO RELATED APPLICATIONS

This patent application claims priority to, and incorporates by reference in its entirety, pending U.S. Provisional Patent Application No. 61/723,703, entitled "System and Method for Fall and/or Concussion Prevention", filed on Nov. 7, 2012.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a system and method for fall and/or concussion prediction. More particularly, the invention relates to a system that utilizes an interactive game, a virtual reality scenario, and/or an immersive graphic environment controlled by the motion of a subject in order to assess the probability that the subject will fall and/or has sustained a concussion. The invention further relates to a method comprising a dual task protocol used to assess the probability that the subject will fall and/or has sustained a concussion.

2. Background

People maintain their upright posture and balance using inputs from proprioceptive, vestibular and visual systems. During normal daily activity, where dynamic balance is to be maintained, other factors also matter. These factors are visual acuity, reaction time, and muscle strength. Visual acuity is important to see a potential danger. Reaction time and muscle strength are important to be able to recover from a potential fall.

There is a direct correlation between a person's risk of falling and the aforementioned factors that contribute to maintaining dynamic balance. For example, if an individual has decreased visual acuity and a slower reaction time, then he or she is more likely to sustain a fall. In addition, if an individual has reduced muscle strength, he or she is also more likely to fall.

Moreover, concussed people have a reduced ability to maintain balance, as well as a reduced capacity to respond to mental challenges. Typical tests for concussion involve either counting number of "falls" or errors in a challenging standing position, or assessing the person's ability to process mental tasks. It is also established that combining the two types of tests known as "dual tasking" gives more reliable results. Each subject is scored in comparison to a baseline performance.

What is needed, therefore, is a system and method for fall and/or concussion prediction that can be used to accurately assess a person's risk for falling and/or predict whether or not a person has sustained a concussion. Moreover, a system and method for fall and/or concussion prediction is needed that measures the ability of a person to move his or her feet and shift his or her weight in response to visual cues. Furthermore, a need exists for a system and method for fall and/or concussion prediction that tests the dynamic balance of an individual by requiring the person to maintain his or her balance by shifting his or her weight in response to visual inputs that require mental processing.

BRIEF SUMMARY OF THE INVENTION

Accordingly, the present invention is directed to a system and method for fall and/or concussion prediction that substantially obviates one or more problems resulting from the limitations and deficiencies of the related art.

In accordance with one aspect of the present invention, there is provided a fall and/or concussion prediction system that includes: a measurement assembly configured to receive a subject, the measurement assembly having a surface for receiving at least one portion of a body of a subject and at least one measurement device, the at least one measurement device configured to sense one or more measured quantities and output one or more signals that are generated based upon the subject's contact with the surface; a visual display device, the visual display device configured to display an interactive game, a virtual reality scenario, and/or an immersive graphic environment that is visible to the subject; and a data processing device operatively coupled to the at least one measurement device of the measurement assembly and the visual display device, the data processing device configured to receive the one or more signals that are generated based upon the subject's contact with the surface of the measurement assembly and to compute one or more numerical values using the one or more signals, the data processing device being configured to control the movement of at least one manipulatable element of the interactive game, the virtual reality scenario, and/or the immersive graphic environment displayed on the visual display device by using the one or more computed numerical values, the data processing device further configured to quantify a subject's performance while playing the interactive game, or while interacting with the virtual reality scenario and/or the immersive graphic environment, using one or more performance parameters, and to assess the probability that the subject will fall and/or predict whether or not the subject has sustained a concussion by using the one or more performance parameters.

In a further embodiment of this aspect of the present invention, the one or more performance parameters are indicative of the subject's balance, visual acuity, and reaction time.

In yet a further embodiment, a difficulty level of the interactive game, the virtual reality scenario, and/or the immersive graphic environment progressively increases over time.

In still a further embodiment, the at least one manipulatable element is capable of affecting the motion of an object as it moves across the visual display device.

In yet a further embodiment, the object moves increasingly faster across the visual display device as the interactive game, the virtual reality scenario, and/or the immersive graphic environment progresses over time.

In still a further embodiment, the at least one manipulatable element comprises a first manipulatable element and a second manipulatable element, the first manipulatable element and the second manipulatable element each being capable of affecting the motion of the object as it moves across the visual display device.

In yet a further embodiment, the first manipulatable element and the second manipulatable element are disposed on generally opposite sides of the visual display device.

In still a further embodiment, the measurement assembly comprises a force measurement assembly, and the one or more numerical values computed using the one or more signals comprise x and y coordinates specifying the center of pressure of a force vector applied by the subject on the force measurement assembly, wherein a value of the x coordinate of the center of pressure determines which one of the first manipulatable element and the second manipulatable element is active, and a value of the y coordinate of the center of pressure determines a translational movement of an active one of the first manipulatable element and the second manipulatable element.

In yet a further embodiment, the measurement assembly comprises one of a force measurement assembly, a pressure measurement assembly, and a contact or timing measurement assembly; and wherein the at least one measurement device comprises one of a force transducer, a pressure transducer, and a contact or timing switch.

In accordance with another aspect of the present invention, there is provided a fall and/or concussion prediction system that includes: a measurement assembly configured to receive a subject, the measurement assembly having a first measurement surface for receiving a first portion of a body of a subject, a second measurement surface for receiving a second portion of a body of a subject, at least one first measurement device, the at least one first measurement device configured to sense one or more measured quantities and output one or more first signals that are generated based upon the subject's contact with the first measurement surface, and at least one second measurement device, the at least one second measurement device configured to sense one or more measured quantities and output one or more second signals that are generated based upon the subject's contact with the second measurement surface; a visual display device, the visual display device configured to display an interactive game, a virtual reality scenario, and/or an immersive graphic environment that is visible to the subject; and a data processing device operatively coupled to the first and second measurement devices of the measurement assembly and the visual display device, the data processing device configured to receive the one or more first signals that are generated based upon the subject's contact with the first measurement surface and compute one or more first numerical values using the one or more first signals, the data processing device being configured to receive the one or more second signals that are generated based upon the subject's contact with the second measurement surface and compute one or more second numerical values using the one or more second signals, the data processing device further configured to control the movement of a first manipulatable element of the interactive game, the virtual reality scenario, and/or the immersive graphic environment displayed on the visual display device by using the one or more first numerical values, and to control the movement of a second manipulatable element of the interactive game, the virtual reality scenario, and/or the immersive graphic environment displayed on the visual display device by using the one or more second numerical values, the data processing device additionally configured to quantify a subject's performance while playing the interactive game, or while interacting with the virtual reality scenario and/or the immersive graphic environment, using one or more performance parameters, and to assess the probability that the subject will fall and/or predict whether or not the subject has sustained a concussion by using the one or more performance parameters.

In a further embodiment of this aspect of the present invention, the one or more performance parameters are indicative of the subject's balance, visual acuity, and reaction time.

In yet a further embodiment, the first manipulatable element and the second manipulatable element are each capable of affecting the motion of an object as it moves across the visual display device.

In still a further embodiment, the object moves increasingly faster across the visual display device as the interactive game, the virtual reality scenario, and/or the immersive graphic environment progresses over time.

In yet a further embodiment, the first manipulatable element and the second manipulatable element are disposed on generally opposite sides of the visual display device.

In still a further embodiment, the measurement assembly comprises a force measurement assembly, and the one or more first numerical values computed using the one or more first signals include a magnitude of the force applied to the first measurement surface by the subject, the one or more second numerical values computed using the one or more second signals include a magnitude of the force applied to the second measurement surface by the subject, and wherein a comparison between the magnitudes of the forces applied to the first and second measurement surfaces by the subject determines which one of the first manipulatable element and the second manipulatable element is active.

In yet a further embodiment, the measurement assembly comprises a force measurement assembly, and the one or more first numerical values computed using the one or more first signals further include a coordinate specifying a location of a first force vector applied by the subject on the first measurement surface, the one or more second numerical values computed using the one or more second signals further include a coordinate specifying a location of a second force vector applied by the subject on the second measurement surface, wherein a value of the coordinate of the first force vector determines a translational movement of the first manipulatable element and a value of the coordinate of the second force vector determines a translational movement of the second manipulatable element.

In still a further embodiment, the measurement assembly comprises one of a force measurement assembly, a pressure measurement assembly, and a contact or timing measurement assembly; and wherein the at least one first measurement device and the at least one second measurement device each comprise one of a force transducer, a pressure transducer, and a contact or timing switch.

In accordance with yet another aspect of the present invention, there is provided a method for fall and/or concussion prediction, the method comprising the steps of: (i) providing a measurement assembly configured to receive a subject thereon, the measurement assembly including: a surface for receiving at least one portion of a body of a subject, and at least one measurement device, the at least one measurement device configured to sense one or more measured quantities and output one or more signals that are generated based upon the subject's contact with the surface; (ii) providing a visual display device configured to display a scene of a first task that is visible to the subject; (iii) providing a data processing device operatively coupled to the at least one measurement device of the measurement assembly and the visual display device; (iv) positioning the subject on the measurement assembly; (v) displaying the scene of the first task on the visual display device so that it is visible to the subject; (vi)

instructing the subject to perform a first task, which relates to the scene on the visual display device, and a second task, which comprises one or more movements on the surface of the measurement assembly; (vii) sensing, by utilizing the at least one measurement device, one or more measured quantities and outputting one or more signals that are generated based upon the subject's contact with the surface of the measurement assembly; (viii) receiving, at the data processing device, the one or more signals that are generated based upon the subject's contact with the surface of the measurement assembly; (ix) computing, by using the data processing device, one or more numerical values from the one or more signals outputted by the at least one measurement device; (x) quantitatively determining, by using the data processing device, a subject's performance during the first and second tasks, the assessment of the subject's performance of the second task being based at least partially upon the one or more numerical values, the subject's performance of the first task being quantitatively expressed in terms of one or more first performance values and the subject's performance of the second task being quantitatively expressed in terms of one or more second performance values; and (xi) determining the probability that the subject will fall and/or predicting whether or not the subject has sustained a concussion by using at least one of the one or more first and second performance values.

In a further embodiment of this aspect of the present invention, the first task comprises a cognitive task and the second task comprises a motor or muscular task.

In yet a further embodiment, the one or more first performance parameters for assessing the subject's performance of the cognitive task comprise one or more of the following: (i) a reaction time of the subject and (ii) an accuracy value for the subject in performing one or more exercises of the cognitive task.

In still a further embodiment, the one or more second performance parameters for assessing the subject's performance of the motor or muscular task comprise one or more of the following: (i) a reaction time of the subject, (ii) a mean movement time of the subject, (iii) a mean movement time difference of the subject, (iv) a sway range of the center of pressure of a force vector applied by the subject on the measurement assembly, (v) a velocity of the center of pressure of a force vector applied by the subject on the measurement assembly, (vi) a sway range of the center of gravity of the subject, and (vii) a velocity of the center of gravity of the subject.

In yet a further embodiment, the first cognitive task comprises one or more of the following: (i) answering a series of multiple choice questions, (ii) identifying a particular letter or letters that have a logical relationship to a predetermined letter or pattern of letters, (iii) identifying a particular number or numbers that have a logical relationship to a predetermined number or pattern of numbers, and (iv) identifying a particular symbol or symbols that have a logical relationship to a predetermined symbol or pattern of symbols.

In still a further embodiment, the second motor or muscular task comprises one or more of the following: (i) walking or running a predetermined distance, (ii) maintaining a static position, (iii) maintaining balance on a moving surface, (iv) balancing one or more objects, (v) moving from a standing position to a seated position, (vi) moving from a seated position to a standing position, (vii) stepping up and over a predetermined obstruction, and (viii) stepping up and down on and off a predetermined obstruction.

In yet a further embodiment, the measurement assembly comprises one of a force measurement assembly, a pressure measurement assembly, and a contact or timing measurement assembly; and wherein the at least one measurement device comprises one of a force transducer, a pressure transducer, and a contact or timing switch.

It is to be understood that the foregoing summary and the following detailed description of the present invention are merely exemplary and explanatory in nature. As such, the foregoing summary and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF THE PREFERRED EMBODIMENT(S) OF THE INVENTION

Figure 1:
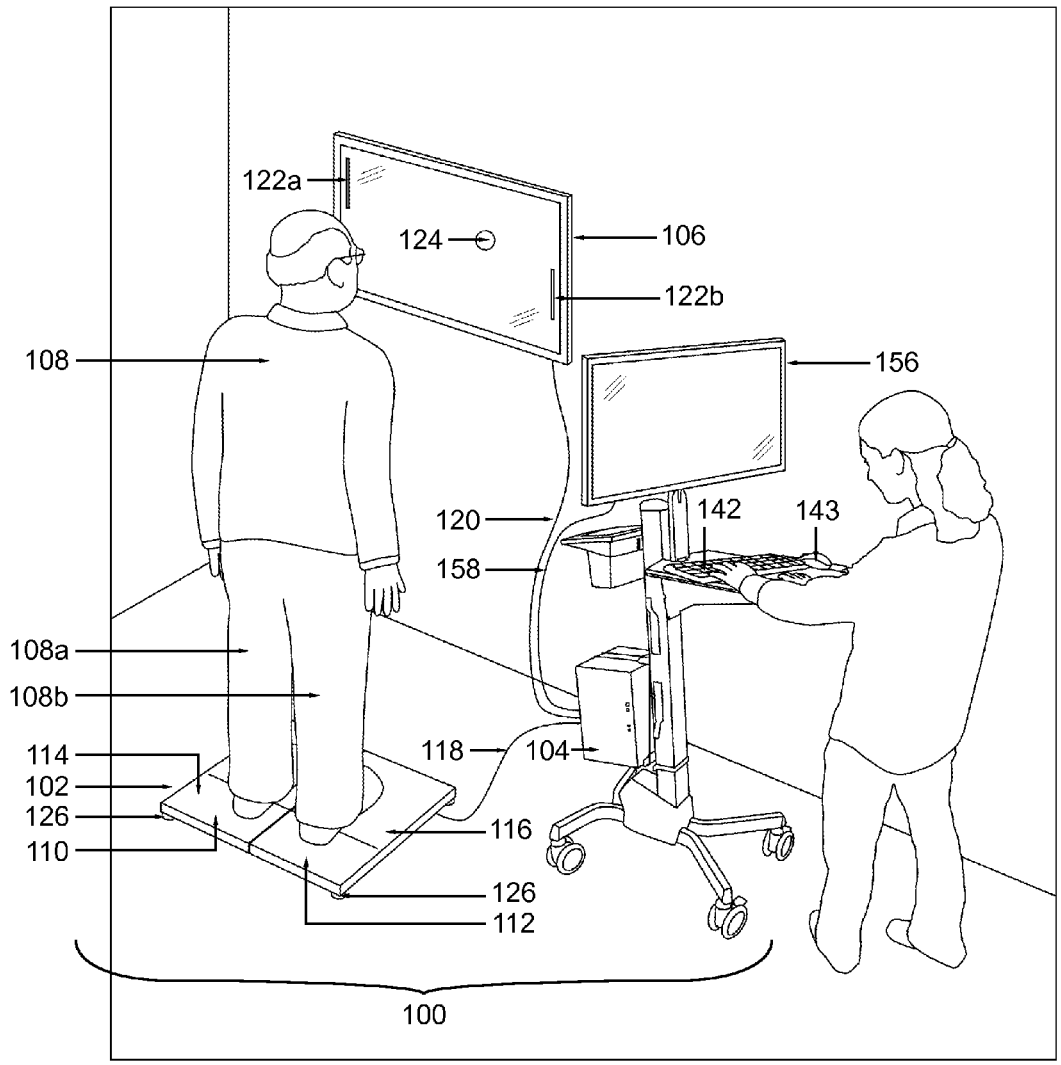
FIG. 1 is a diagrammatic perspective view of a system for fall and/or concussion prediction according to an embodiment of the invention, wherein an interactive game is being displayed on the subject visual display device.

An exemplary embodiment of the fall and/or concussion prediction system is seen generally at 100 in FIG. 1. The fall and/or concussion prediction system 100 generally comprises a force measurement assembly 102 that is operatively coupled to a data acquisition/data processing device 104 (i.e., a computing device that is capable of collecting, storing, and processing data), which in turn, is operatively coupled to a subject visual display device 106 and an operator visual display device 156. As illustrated in FIG. 1, the force measurement assembly 102 is configured to receive a subject 108 thereon, and is capable of measuring the forces and/or moments applied to its measurement surfaces 114, 116 by the subject 108. Advantageously, providing two visual display devices 106, 156, allows both the subject 108 and the clinician to have dedicated visual display devices (e.g., movement cues can be displayed on the subject visual display device 106, while the subject's performance is observed by the clinician on the operator visual display device 156).

As shown in FIG. 1, the data acquisition/data processing device 104 includes a plurality of user input devices 142, 143 connected thereto. Preferably, the user input devices 142, 143 comprise a keyboard 142 and a mouse 143. In addition, the operator visual display device 156 may also serve as a user input device if it is provided with touch screen capabilities. While a desktop type computing system is depicted in FIG. 1, one of ordinary of skill in the art will appreciate that another type of data acquisition/data processing device 104 can be substituted for the desktop computing system such as, but not limited to, a laptop or a palmtop computing device (i.e., a PDA). In addition, rather than providing a data acquisition/data processing device 104, it is to be understood that only a data acquisition device could be provided without departing from the spirit and the scope of the claimed invention.

In one embodiment, the fall and/or concussion prediction system 100 is only provided with the subject visual display device 106. The operator visual display device 156 is not provided in this embodiment. In this embodiment, the visual display device 106 could be used by the operator or clinician as well as the subject.

As illustrated in FIG. 1, force measurement assembly 102 is operatively coupled to the data acquisition/data processing device 104 by virtue of an electrical cable 118. In one embodiment of the invention, the electrical cable 118 is used for data transmission, as well as for providing power to the force measurement assembly 102. Various types of data transmission cables can be used for cable 118. For example, the cable 118 can be a Universal Serial Bus (USB) cable or an Ethernet cable. Preferably, the electrical cable 118 contains a plurality of electrical wires bundled together, with at least one wire being used for power and at least another wire being used for transmitting data. The bundling of the power and data transmission wires into a single electrical cable 118 advantageously creates a simpler and more efficient design. In addition, it enhances the safety of the testing environment when human subjects are being tested on the force measurement assembly 102. However, it is to be understood that the force measurement assembly 102 can be operatively coupled to the data acquisition/data processing device 104 using other signal transmission means, such as a wireless data transmission system. If a wireless data transmission system is employed, it is preferable to provide the force measurement assembly 102 with a separate power supply in the form of an internal power supply or a dedicated external power supply.

Referring again to FIG. 1, it can be seen that the force measurement assembly 102 of the illustrated embodiment is in the form of a dual force plate assembly. The dual force plate assembly includes a first plate component 110, a second plate component 112, at least one force transducer associated with the first plate component 110, and at least one force transducer associated with the second plate component 112. In the illustrated embodiment, a subject 108 stands in an upright position on the force measurement assembly 102 and each foot of the subject 108 is placed on the top surfaces 114, 116 of a respective plate component 110, 112 (i.e., one foot on the top surface 114 of the first plate component 110 and the other foot on the top surface 116 of the second plate component 112). The at least one force transducer associated with the first plate component 110 is configured to sense one or more measured quantities and output one or more first signals that are representative of forces and/or moments being applied to its measurement surface 114 by the left foot/leg 108*a* of the subject 108, whereas the at least one force transducer associated with the second plate component 112 is configured to sense one or more measured quantities and output one or more second signals that are representative of forces and/or moments being applied to its measurement surface 116 by the right foot/leg 108*b* of subject 108.

Figure 5:
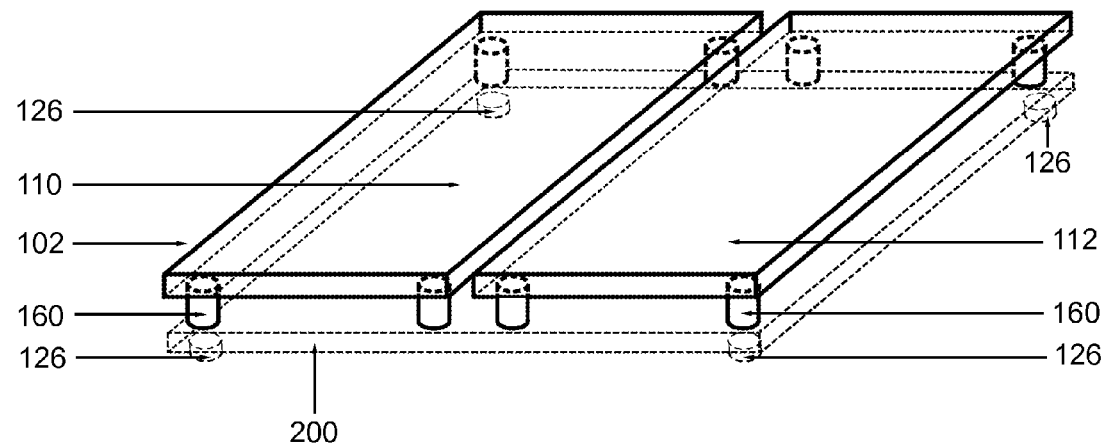
FIG. 5 is a diagrammatic perspective view of one force measurement assembly used in the fall and/or concussion prediction system, according to an embodiment of the invention, wherein the force measurement assembly is in the form of a dual force plate.

In the illustrated embodiment, the at least one force transducer associated with the first and second plate components 110, 112 comprises four (4) pylori-type force transducers 160 (or pylori-type load cells) that are disposed underneath, and near each of the four corners (4) of the first plate component 110 and the second plate component 112 (see FIG. 5). Each of the eight (8) illustrated pylori-type force transducers 160 has a plurality of strain gages adhered to the outer periphery of a cylindrically-shaped force transducer sensing element for detecting the mechanical strain of the force transducer sensing element imparted thereon by the force(s) applied to the surfaces of the force measurement assembly 102. As shown in FIG. 5, a base plate 200 can be provided underneath the transducers 160 of each plate component 110, 112. In some embodiments, the feet 126 are mounted on the bottom surface of this base plate 200. Also, in some embodiments, side plates are mounted between the base plate 200 and the plate components 110, 112 so as to conceal the force transducers 160.

In an alternative embodiment, rather than using four (4) pylori-type force transducers 160 on each plate component 110, 112, force transducers in the form of transducer beams could be provided under each plate component 110, 112. In this alternative embodiment, the first plate component 110 could comprise two transducer beams that are disposed underneath, and on generally opposite sides of the first plate component 110. Similarly, in this embodiment, the second plate component 112 could comprise two transducer beams that are disposed underneath, and on generally opposite sides of the second plate component 112. Similar to the pylori-type force transducers 160, the force transducer beams could have a plurality of strain gages attached to one or more surfaces thereof for sensing the mechanical strain imparted on the beam by the force(s) applied to the surfaces of the force measurement assembly 102.

Also, as shown in FIG. 1, the force measurement assembly 102 is provided with a plurality of support feet 126 disposed thereunder. Preferably, each of the four (4) corners of the force measurement assembly 102 is provided with a support foot 126. In some embodiment(s), each support foot 126 is attached to a bottom surface of a force transducer or a base plate. In another embodiment, one or more of the force transducers could function as support feet (e.g., if pylori-type force transducers are used, the first and second plate components 110, 112 could be supported on the force transducers). In one preferred embodiment, at least one of the support feet 126 is adjustable so as to facilitate the leveling of the force measurement assembly 102 on an uneven floor surface.

Figure 2:
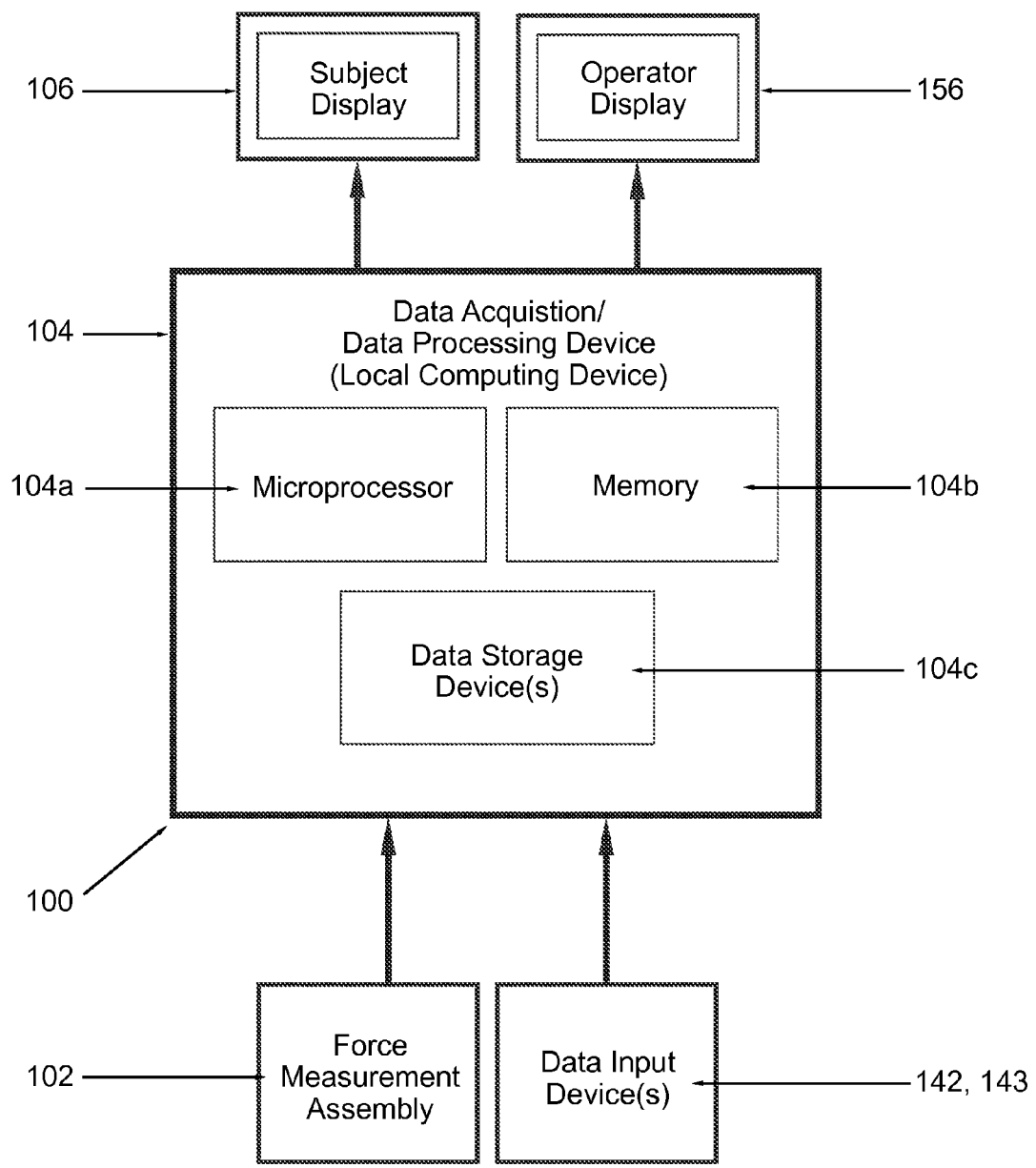
FIG. 2 is a block diagram of constituent components of the fall and/or concussion prediction system, according to an embodiment of the invention.

Now, turning to FIG. 2, it can be seen that the data acquisition/data processing device 104 of the fall and/or concussion prediction system 100 comprises a microprocessor 104*a* for processing data, memory 104*b* (e.g., random access memory or RAM) for storing data during the processing thereof, and data storage device(s) 104*c*, such as one or more hard drives, compact disk drives, floppy disk drives, flash drives, or any combination thereof. As shown in FIG. 2, the force measurement assembly 102, the subject visual display device 106, and the operator visual display device 156 are operatively coupled to the data acquisition/data processing device 104 such that data is capable of being transferred between these devices 102, 104, 106, and 156. Also, as illustrated in FIG. 2, a plurality of user data input devices, such as a keyboard 142 and a mouse 143, are operatively coupled to the data acquisition/data processing device 104 so that a user is able to enter data into the data acquisition/data processing device 104. In some embodiments, the data acquisition/data processing device 104 can be in the form of a desktop computer, while in other embodiments, the data acquisition/data processing device 104 can be embodied as a laptop computer.

Figure 4:
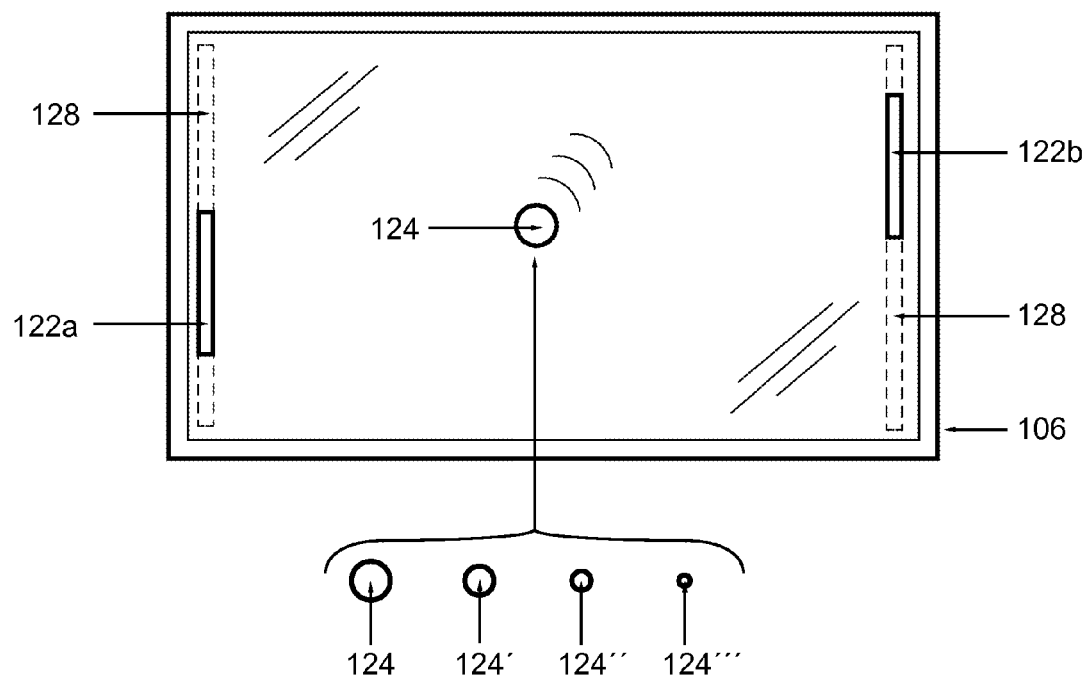
FIG. 4 is a diagrammatic frontal view of the subject visual display device of the fall and/or concussion prediction system with an exemplary interactive game displayed thereon, according to an embodiment of the invention.

With reference to FIGS. 1 and 4, the subject visual display device 106 of the fall and/or concussion prediction system 100 will be described in more detail. In the illustrated embodiment, the subject visual display device 106 and the operator visual display device 156 are each in the form of a flat panel monitor. The subject visual display device 106 is operatively coupled to the data acquisition/data processing device 104 by means of data transmission cable 120, while the operator visual display device 156 is operatively coupled to the data acquisition/data processing device 104 by means of data transmission cable 158. Those of ordinary skill in the art will readily appreciate that various types of flat panel monitors having various types of data transmission cables 120, 158 may be used to operatively couple the subject visual display device 106 and the operator visual display device 156 to the data acquisition/data processing device 104. For example, the flat panel monitor employed may utilize a video graphics array (VGA) cable, a digital visual interface (DVI or DVI-D) cable, a high-definition multimedia interface (HDMI or Mini-HDMI) cable, or a DisplayPort digital display interface cable to connect to the data acquisition/data processing device 104. Alternatively, in other embodiments of the invention, the subject visual display device 106 and/or operator visual display device 156 can be operatively coupled to the data acquisition/data processing device 104 using wireless data transmission means. Electrical power is supplied to the subject visual display device 106 and/or the operator visual display device 156 using a separate power cord that connects to a building wall receptacle.

Those of ordinary skill in the art will appreciate that the subject visual display device 106 can be embodied in various forms. For example, if the subject visual display device 106 is in the form of a flat screen monitor as illustrated in FIG. 1, it may comprise a liquid crystal display (i.e., an LCD display), a light-emitting diode display (i.e., an LED display), a plasma display, a projection-type display, or a rear projection-type display. Although, it will be appreciated that the subject visual display device 106 may take other forms as well, such as a head-mounted display, a heads-up display, or a 3-dimensional display. The subject visual display device 106 may also be in the form of a touch pad display. The operator visual display device 156 may be embodied in various forms as well (e.g., an LCD display, an LED display, a plasma display, etc.).

Figure 3:
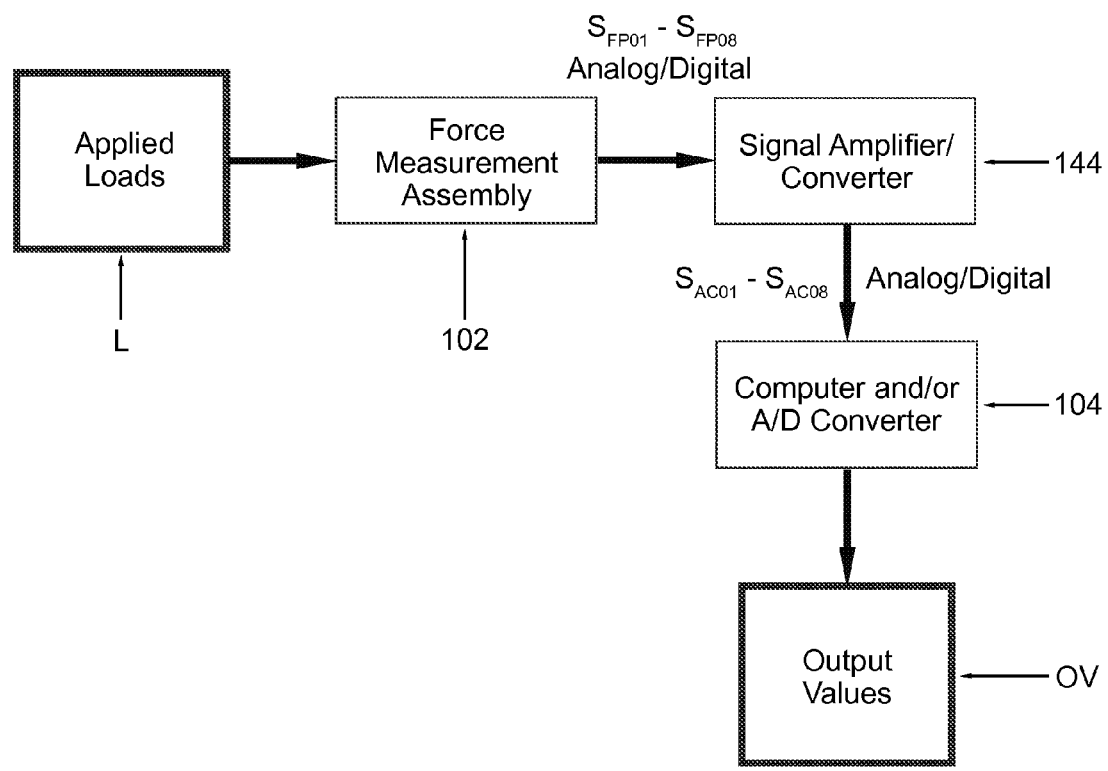
FIG. 3 is a block diagram illustrating data manipulation operations carried out by the fall and/or concussion prediction system, according to an embodiment of the invention.

FIG. 3 graphically illustrates the acquisition and processing of the load data carried out by the exemplary embodiment of the fall and/or concussion prediction system 100. Initially, as shown in FIG. 3, a load L is applied to the force measurement assembly 102 by a subject disposed thereon. The load is transmitted from the first and second plate components 110, 112 to its respective set of pylori-type force transducers 160 or force transducer beams. As described above, in one embodiment of the invention, each plate component 110, 112 comprises four (4) pylori-type force transducers 160 disposed thereunder (e.g., see FIG. 5). Preferably, these pylori-type force transducers are disposed near respective corners of each plate component 110, 112. In a preferred embodiment of the invention, each of the pylori-type force transducers 160 includes a plurality of strain gages wired in one or more Wheatstone bridge configurations, wherein the electrical resistance of each strain gage is altered when the associated portion of the associated pylori-type force transducer undergoes deformation (i.e., a measured quantity) resulting from the load (i.e., forces and/or moments) acting on the first and second plate components 110, 112. For each plurality of strain gages disposed on the pylori-type force transducers 160, the change in the electrical resistance of the strain gages brings about a consequential change in the output voltage of the Wheatstone bridge (i.e., a quantity representative of the load being applied to the measurement surface). Thus, in one embodiment, the four (4) pylori-type force transducers 160 disposed under each plate component 110, 112 output a total of four (4) analog output voltages (signals). In another embodiment, the four (4) pylori-type force transducers 160 disposed under each plate component 110, 112 output a combined total of three (3) analog output voltages (signals). In some embodiments, the three (3) or four (4) analog output voltages from each plate component 110, 112 are then transmitted to a preamplifier board (not shown) for preconditioning. The preamplifier board is used to increase the magnitudes of the transducer analog voltages, and preferably, to convert the analog voltage signals into digital voltage signals as well. After which, the force measurement assembly 102 transmits the force plate output signals $S_{FPO1}$-$S_{FPO8}$ to a main signal amplifier/converter 144. Depending on whether the preamplifier board also includes an analog-to-digital (A/D) converter, the force plate output signals $S_{FPO1}$-$S_{FPO8}$ could be either in the form of analog signals or digital signals. The main signal amplifier/converter 144 further magnifies the force plate output signals $S_{FPO1}$-$S_{FPO8}$, and if the signals $S_{FPO1}$-$S_{FPO8}$ are of the analog-type (for a case where the preamplifier board did not include an analog-to-digital (A/D) converter), it may also convert the analog signals to digital signals. Then, the signal amplifier/converter 144 transmits either the digital or analog signals $S_{ACO1}$-$S_{ACO8}$ to the data acquisition/data processing device 104 (computer or computing device 104) so that the forces and/or moments that are being applied to the surfaces of the force measurement assembly 102 can be transformed into output values OV that can be used in the interactive game of the fall and/or concussion prediction system 100. In addition to the components 104a, 104b, 104c, the data acquisition/data processing device 104 may further comprise an analog-to-digital (A/D) converter if the signals $S_{ACO1}$-$S_{ACO8}$ are in the form of analog signals. In such a case, the analog-to-digital converter will convert the analog signals into digital signals for processing by the microprocessor 104a.

When the data acquisition/data processing device 104 receives the voltage signals $S_{ACO1}$-$S_{ACO8}$, it initially transforms the signals into output forces and/or moments by multiplying the voltage signals $S_{ACO1}$-$S_{ACO8}$ by a calibration matrix. After which, the force $F_L$ exerted on the surface of the first force plate by the left foot of the subject, the force $F_R$ exerted on the surface of the second force plate by the right foot of the subject, and the center of pressure for each foot of the subject (i.e., the x and y coordinates of the point of application of the force applied to the measurement surface by each foot) are determined by the data acquisition/data processing device 104. The computations performed in the determination of the forces and center of pressure are described hereinafter.

While, in the exemplary embodiment described hereinafter, the data acquisition/data processing device 104 determines the vertical forces $F_{Lz}$, $F_{Rz}$ exerted on the surface of the first and second force plates by the feet of the subject and the center of pressure for each foot of the subject, it is to be understood that the invention is not so limited. Rather, in other embodiments of the invention, the output forces of the data acquisition/data processing device 104 could include all three (3) orthogonal components of the resultant forces acting on the two plate components 110, 112. In yet other embodiments of the invention, the output forces and moments of the data acquisition/data processing device 104 can be in the form of other forces and moments as well.

Now, the functionality of the fall and/or concussion prediction system 100 will be described in detail. It is to be understood that the aforedescribed functionality of the fall and/or concussion prediction system 100 can be carried out by the data acquisition/data processing device 104 utilizing software, hardware, or a combination of both hardware and software. For example, the data acquisition/data processing device 104 can be specially programmed to carry out the functionality described hereinafter. In one embodiment of the invention, the computer program instructions necessary to carry out this functionality may be loaded directly onto an internal data storage device 104c of the data acquisition/data processing device 104 (e.g., on a hard drive thereof) and subsequently executed by the microprocessor 104a of the data acquisition/data processing device 104. Alternatively, these computer program instructions could be stored on a portable computer-readable medium (e.g., a flash drive, a floppy disk, a compact disk, etc.), and then subsequently loaded onto the data acquisition/data processing device 104 such that the instructions can be executed thereby. In other embodiments, these computer program instructions could be embodied in the hardware of the data acquisition/data processing device 104, rather than in the software thereof. It is also possible for the computer program instructions to be embodied in a combination of both the hardware and the software.

In the illustrated embodiment, the data acquisition/data processing device 104 is configured to control the movement of a first game element (or first manipulatable element) of an interactive game displayed on the subject visual display device 106 by using one or more first numerical values determined from the output signals of the force transducers associated with the first plate component 110. Similarly, the data acquisition/data processing device 104 is configured to control the movement of a second game element (or second manipulatable element) of an interactive game displayed on the subject visual display device 106 by using one or more second numerical values determined from the output signals of the force transducers associated with the second plate component 112. Referring to FIGS. 1 and 4, it can be seen that the first and second game elements may comprise generally oppositely disposed paddles 122a, 122b for affecting the motion of an object (e.g., a ball 124) as it moves across the subject visual display device 106. As shown in FIG. 4, the paddles 122a, 122b are capable of translating along a generally vertical path 128. In the illustrative embodiment, the paddles 122a, 122b are displaced generally up or down to contact the ball 124, and to change its movement from an generally outward direction of travel (e.g., towards a lateral side of the subject visual display device 106) to a generally inward direction of travel (e.g., towards the middle of the subject visual display device 106 or diagonally towards the top or bottom edge of the subject visual display device 106). In this manner, a subject tries to continually contact the ball 124 before it reaches the lateral boundary of the subject visual display device 106. As such, the illustrated interactive game comprises the back-and-forth motion of the ball 124 between the two paddles 122a, 122b.

In a preferred embodiment, the object (e.g., ball 124) that is displaced across the subject visual display device 106, and the direction of which is altered by the paddles 122a, 122b, moves increasingly faster across the subject visual display device 106 as the interactive game progresses. For example, as the subject plays the interactive game, the speed at which the ball 124 travels across the subject visual display device 106 increases steadily over time. In one embodiment, the speed of the ball 124 might increase linearly over time, while in another embodiment, the speed of the ball 124 could increase exponentially over time. Advantageously, increasing the speed at which the ball 124 travels across the subject visual display device 106 makes the interactive game increasingly more challenging to the subject (i.e., the difficulty level of the interactive game increases), thereby enabling the fall and/or concussion prediction system 100 to assess a subject's ability to adapt to changing conditions over time. The speed of the ball 124 could be adjusted in accordance with a system of game levels (e.g., during game level 1, the ball 124 travels at a first predetermined speed, during game level 2, the ball 124 travels at a second, higher predetermined speed, during game level 3, the ball 124 travels at a third, still higher predetermined speed, etc.).

Also, in one or more embodiments of the invention, the object (e.g., ball 124) could steadily decrease in size (i.e., ball 124 becomes continually smaller) over the course of the game (i.e., different balls 124', 124", 124'" have smaller sizes—see FIG. 4). Advantageously, like increasing the speed at which the ball 124 travels, decreasing the physical size of the ball also makes the interactive game increasingly more challenging to the subject (i.e., the difficulty level of the interactive game increases) over time, thereby enabling the fall and/or concussion prediction system 100 to assess a subject's ability to adapt to changing conditions over time. In particular, steadily decreasing the size of the ball 124 over time would effectively test a subject's visual acuity because subjects having certain visual disorders or decreased visual perception would likely have difficulty seeing the ball 124 once it was decreased to a certain size. As for the speed of the ball 124, the size of the ball 124 could be adjusted in accordance with a system of game levels (e.g., during game level 1, the ball 124 has a first predetermined size, during game level 2, the ball 124 has a second, smaller predetermined size, during game level 3, the ball 124 has a third, still smaller predetermined size, etc.).

In one or more embodiments, the one or more first numerical values determined from the output signals of the force transducers associated with the first plate component 110 include a magnitude of the force (e.g., magnitude of left vertical force $F_{Z_L}$) applied to the first measurement surface 114 of the first plate component 110 (e.g., left plate) by the subject. Similarly, the one or more second numerical values determined from the output signals of the force transducers associated with the second plate component 112 include a magnitude of the force (e.g., magnitude of right vertical force $F_{Z_R}$) applied to the second measurement surface 116 of the second plate component 112 (e.g., right plate) by the subject. The left and right vertical forces $F_{Z_L}$, $F_{Z_R}$ are determined by multiplying the voltage signals from the transducers of the corresponding force plates by the calibration matrix for the force measurement assembly 102. Once the magnitudes of the left and right vertical forces $F_{Z_L}$, $F_{Z_R}$ are computed, the magnitudes are compared so as to determine which one of the first game element (e.g., left paddle 122a) and the second game element (e.g., right paddle 122b) is active. For example, when the left vertical force $F_{Z_L}$ is noticeably greater that the right vertical force $F_{Z_R}$, the left paddle 122a will be active and the right paddle 122b will be inactive (e.g., when the magnitude of the left vertical force is at least 1.05 times greater than the magnitude of the right vertical force, then the left paddle 122a will be active and the right paddle 122b will be inactive). As such, the subject is able to selectively activate one of the left and right paddles 122a, 122b by shifting weight accordingly (i.e. to the left plate or to the right plate). It is to be understood that, in other embodiments of the invention, the magnitude of the total left and right force $\vec{F}_L$, $\vec{F}_R$ is used in lieu of the left and right vertical forces $F_{Z_L}$, $F_{Z_R}$ (e.g., in a 6-component force measurement device).

Also, in one or more embodiments, the one or more first numerical values determined from the output signals of the force transducers associated with the first plate component 110 further include x and y coordinates (e.g., coordinates $x_{P_L}$, $y_{P_L}$) specifying the center of pressure of a first force vector (e.g., left force vector $\vec{F}_L$) applied by the subject to the first measurement surface 114 of the first plate component 110 (e.g., left plate) by the subject. Similarly, the one or more second numerical values determined from the output signals of the force transducers associated with the second plate component 112 further include x and y coordinates (e.g., coordinates $x_{P_R}$, $y_{P_R}$) specifying the center of pressure of a second force vector (e.g., right force vector $\vec{F}_R$) applied by the subject to the second measurement surface 116 of the second plate component 112 (e.g., right plate) by the subject. If the left and right force plates of the force measurement assembly 102 are configured as 3-component force measurement devices (i.e., the transducers of these plates are capable of collectively measuring $F_Z$, $M_x$, $M_y$), then the center of pressure of the first force vector $\vec{F}_L$ applied by the subject to the first measurement surface 114 of the first plate component 110 is computed as follows:

$$x_{P_L} = \frac{-M_{y_L}}{F_{Z_L}} \quad (1)$$

$$y_{P_L} = \frac{M_{x_L}}{F_{Z_L}} \quad (2)$$

where:

$x_{P_L}$, $y_{P_L}$: coordinates of the point of application for the force (i.e., center of pressure) on the first plate component 110 (left force plate);

$F_{Z_L}$: z-component of the resultant force acting on the first plate component 110 (left force plate);

$M_{x_L}$: x-component of the resultant moment acting on the first plate component 110 (left force plate); and $M_{y_L}$: y-component of the resultant moment acting on the first plate component 110 (left force plate).

Similarly, when the left and right force plates of the force measurement assembly 102 are configured as 3-component force measurement devices, the center of pressure of the second force vector $\vec{F}_R$ applied by the subject to the second measurement surface 116 of the second plate component 112 is computed as follows:

$$x_{P_R} = \frac{-M_{y_R}}{F_{Z_R}} \quad (3)$$

$$y_{P_R} = \frac{M_{x_R}}{F_{Z_R}} \quad (4)$$

$x_{P_R}$, $y_{P_R}$: coordinates of the point of application for the force (i.e., center of pressure) on the second plate component 112 (right force plate);

$F_{Z_R}$: z-component of the resultant force acting on the second plate component 112 (right force plate);

$M_{x_R}$ x-component of the resultant moment acting on the second plate component 112 (right force plate); and $M_{y_R}$: y-component of the resultant moment acting on the second plate component 112 (right force plate).

However, if the left and right force plates of the force measurement assembly 102 are configured as 6-component force measurement devices (i.e., the transducers of these plates are capable of collectively measuring $F_x$, $F_y$, $F_z$, $M_x$, $M_y$, $M_z$), then the center of pressure of the first force vector $F_L$ applied by the subject to the first measurement surface 114 of the first plate component 110 is computed as follows:

$$x_{P_L} = \frac{-h_L \cdot F_{x_L} - M_{y_L}}{F_{Z_L}} \quad (5)$$

$$y_{P_L} = \frac{-h_L \cdot F_{y_L} + M_{x_L}}{F_{Z_L}} \quad (6)$$

where:

$h_L$: thickness above the top surface of any material covering the first plate component 110 (left force plate);

$F_{x_L}$: x-component of the resultant force acting on the first plate component 110 (left force plate); and $F_{y_L}$: y-component of the resultant force acting on the first plate component 110 (left force plate).

Similarly, when the left and right force plates of the force measurement assembly 102 are configured as 6-component force measurement devices, the center of pressure of the second force vector $\vec{F}_R$ applied by the subject to the second measurement surface 116 of the second plate component 112 is computed as follows:

$$x_{P_R} = \frac{-h_R \cdot F_{x_R} - M_{y_R}}{F_{Z_R}} \quad (7)$$

$$y_{P_R} = \frac{-h_R \cdot F_{y_R} + M_{x_R}}{F_{Z_R}} \quad (8)$$

where:

$h_R$: thickness above the top surface of any material covering the second plate component 112 (right force plate);

$F_{x_R}$: x-component of the resultant force acting on the second plate component 112 (right force plate); and $F_{y_R}$: y-component of the resultant force acting on the second plate component 112 (right force plate).

After the centers of pressure are computed for the left and right force plates of the force measurement assembly 102, a value of the y coordinate ($y_{P_L}$) of the first force vector (e.g., left force vector $\vec{F}_L$) can be used to determine the translational movement of the first game element (e.g., left paddle 122a), whereas a value of the y coordinate ($y_{P_R}$) of the second force vector (e.g., right force vector $\vec{F}_R$) can be used to determine the translational movement of the second game element (e.g., right paddle 122b). When the y coordinates of each force vector ($\vec{F}_L$, $\vec{F}_R$) are equal to zero, the left and right paddles 122a, 122b are approximately located in the middle of the subject visual display device 106. However, for example, when the y coordinate of the first force vector (e.g., left force vector $\vec{F}_L$) is a positive number (refer to the coordinates axes 130, 132 illustrated in FIG. 6), the left paddle 122a will be displaced upwardly on the screen. Conversely, when the y coordinate of the first force vector (e.g., left force vector $F_L$) is a negative number, the left paddle 122a will be displaced downwardly on the screen. The right paddle 122b will be controlled in a similar manner depending on the value of the y coordinate ($y_{P_R}$) of the second force vector (e.g., right force vector $\vec{F}_R$) determined with respect to coordinate axes 134, 136. It is to be understood that the values of the center of pressure coordinates for the first and second plate components ($x_{P_L}$, $y_{P_L}$, $x_{P_R}$, $y_{P_R}$) vary as the subject moves his or her legs on the first and second plate components 110, 112. As such, the subject is able to selectively control the movement of the left and right paddles 122a, 122b by shifting his or her legs accordingly on the force plates (i.e, forward or backward).

Figure 6:
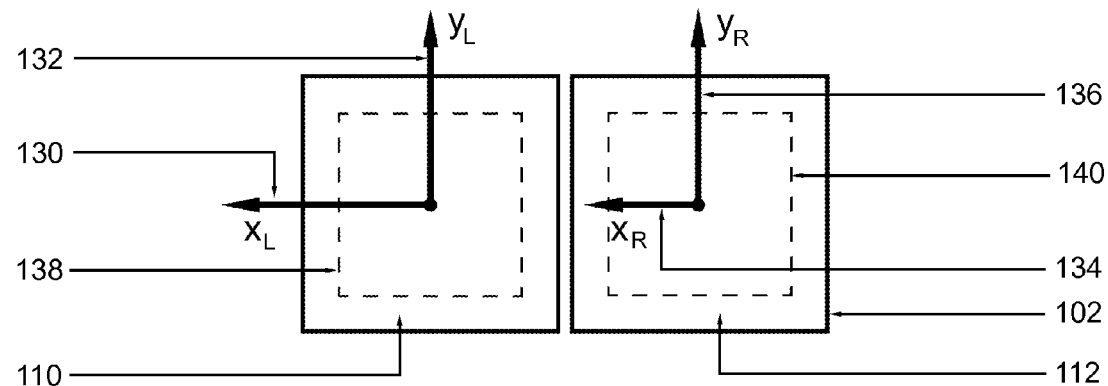
FIG. 6 is a diagrammatic top view of one force measurement assembly used in the fall and/or concussion prediction system with exemplary coordinate axes superimposed thereon, according to an embodiment of the invention, wherein the force measurement assembly is in the form of a dual force plate.

Referring to FIG. 6, it can be seen that the first and second plate components 110, 112 (i.e., left and right force plates) may have respective imaginary inner zones 138, 140 defined on the respective surfaces 114, 116 thereof. The imaginary inner zones 138, 140 define the maximum extents of displacement for paddles 122a, 122b. For example, if the y coordinate ($y_{P_L}$) of the first force vector lies on, or above, the upper dashed line of the zone 138 on first plate component 110, then the left paddle 122a will be displaced to its most upward position (i.e., near the top of subject visual display device 106). Conversely, if the y coordinate ($y_L$) of the first force vector lies on, or below, the lower dashed line of the zone 138 on first plate component 110, then the left paddle 122a will be displaced to its most downward position (i.e., near the bottom of subject visual display device 106). The right paddle 122b is displaced in a similar manner with respect to the location of the y coordinate ($y_{P_R}$) of the second force vector relative to the upper and lower dashed lines of imaginary zone 140 on second plate component 112. The purpose of the imaginary inner zones 138, 140 on the first and second plate components 110, 112 is to define the most comfortable range of motion for the subject disposed on the force measurement assembly 102. Otherwise, if the outermost edges of each plate component 110, 112 corresponded to the maximum displacement positions of the paddles 122a, 122b, it may be very difficult for a subject to achieve these outermost boundaries. It may also pose safety concerns because the subject could inadvertently fall off the force measurement assembly 102 when he or she is attempting to reach these outermost positions.

Rather, than using four (4) force transducer pylons 160 under each plate, or two spaced apart force transducer beams under each plate, it is to be understood that the force measurement assembly 102 can also utilize the force transducer technology described in pending patent application Ser. No. 13/348,506, the entire disclosure of which is incorporated herein by reference. If the force transducer technology described in application Ser. No. 13/348,506 is employed, it is to be understood that the center of pressure coordinates ($x_{P_L}$, $y_{P_L}$, $x_{P_R}$, $y_{P_R}$) alternatively can be computed in the manner described in that application.

Figure 7:
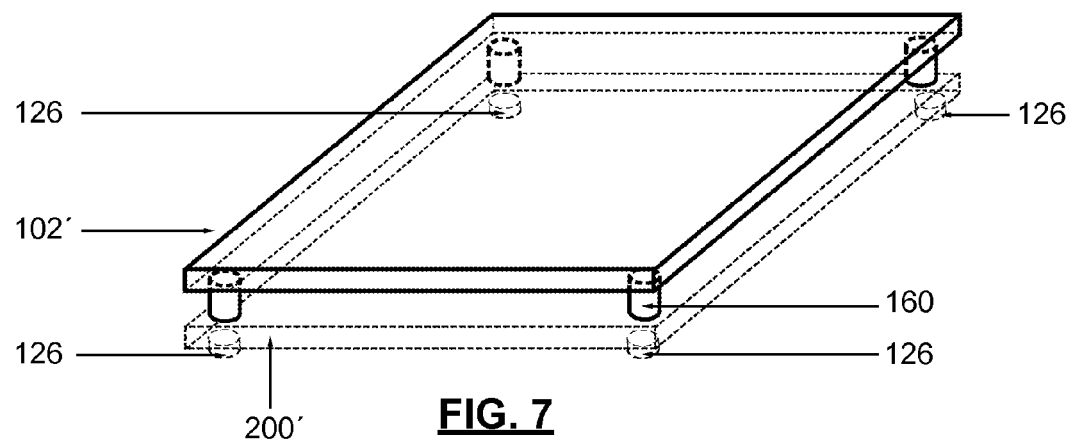
FIG. 7 is a diagrammatic perspective view of another force measurement assembly used in the fall and/or concussion prediction system, according to an embodiment of the invention, wherein the force measurement assembly is in the form of a single force plate.
Figure 8:
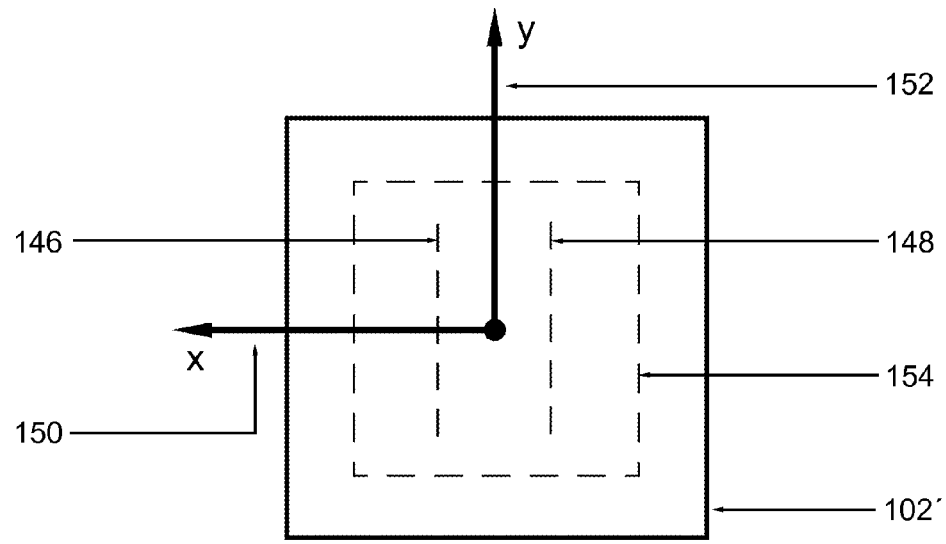
FIG. 8 is a diagrammatic top view of another force measurement assembly used in the fall and/or concussion prediction system with exemplary coordinate axes superimposed thereon, according to an embodiment of the invention, wherein the force measurement assembly is in the form of a single force plate.

In other embodiments of the invention, rather than using a force measurement assembly 102 having first and second plate components 110, 112, it is to be understood that a force measurement assembly 102' in the form of a single force plate may be employed (see FIGS. 7 and 8). Similar to that described above for the dual force plate of FIG. 5, a base plate 200' can be provided underneath the transducers 160 of the single force plate illustrated in FIG. 7. Unlike the dual force plate assembly illustrated in FIG. 1, the single force plate comprises a single measurement surface on which both of a subject's feet are placed during testing. As such, the manner in which first and second game elements (e.g., paddles 122a, 122b) are made active and controlled during the interactive game is different for the single force plate, as compared to the dual force plate assembly of FIG. 1.

As described above for the force measurement assembly 102 in the form of a dual force plate assembly, the one or more numerical values determined from the output signals of the one or more force transducers associated with the single force plate assembly are used to activate, and control the movement of, the first and second game elements (e.g., paddles 122a, 122b). Also, similar to the dual force plate assembly, the one or more numerical values computed using the one or more signals of the force transducer(s) also include x and y coordinates specifying the center of pressure of a force vector applied by the subject on the force measurement assembly. The manner in which the center of pressure coordinates are computed for the single force plate assembly is the same as that described above for a single plate of the dual force plate assembly, except that there will only be a single set of center of pressure coordinates (e.g., coordinates $x_P$, $y_P$) for a single measurement surface, rather than two sets of coordinates ($x_{P_L}$, $y_{P_L}$; $x_{P_R}$, $y_{P_R}$) described above for the two independent measurement surfaces 114, 116 of the dual force plate assembly. For the single force plate assembly, the x coordinate ($x_P$) of the center of pressure determines which one of the first game element (e.g., paddle 122a) and the second game element (e.g., paddle 122b) is active. For example, if the x coordinate of the center of pressure is greater than a predetermined positive value (e.g., as indicated by the dashed line 146 in FIG. 8), then the first game element (e.g., the left paddle 122a) is made active. Conversely, if the x coordinate of the center of pressure is less than a predetermined negative value (e.g., as indicated by the dashed line 148 in FIG. 8), then the second game element (e.g., the right paddle 122b) is made active. Thus, a subject is able to selectively activate a desired one of the game elements (e.g., paddles 122a, 122b) by laterally shifting his or her center of pressure on the surface of the single force plate (i.e., the subject can shift his weight to a selected side of the force plate).

Similar to that described above for the dual force plate assembly (i.e., force measurement assembly 102), the y coordinate ($y_P$) of the center of pressure measured by the force single force plate 102' is used to determine the translational movement of the first and second game elements (e.g., left and right paddles 122a, 122b). First, the subject selects an active one of the two game elements 122a, 122b by laterally shifting his or her weight on the force plate (which results in either a positive or negative value for the x coordinate, $x_P$). Then, after the desired game element 122a, 122b is made active, the subject shifts his or her weight in a forward or backward manner on the single force plate 102'. Similar to the dual force plate embodiment explained above, when the y coordinate of the applied force vector ($\vec{F}$) is equal to zero, the active one of the left and right paddles 122a, 122b is approximately located in the middle of the of the subject visual display device 106. However, for example, when the y coordinate of the force vector (F) is a positive number (refer to the coordinates axes 150, 152 illustrated in FIG. 8), the active one of the paddles 122a, 122b will be displaced upwardly on the screen. Conversely, when the y coordinate of the force vector ($\vec{F}$) is a negative number (refer to the coordinates axes 150, 152 illustrated in FIG. 8), the active one of the paddles 122a, 122b will be displaced downwardly on the screen. It is to be understood that the values of the center of pressure coordinates ($x_P$, $y_P$) vary as the subject moves his or her legs on the single force plate assembly 102'. As such, the subject is able to selectively activate and control the movement of the left and right paddles 122a, 122b by shifting his or her legs accordingly on the force plate (i.e, right or left to change paddles, and forward or backward to move the active paddle). Like the imaginary inner zones 138, 140 of the respective first and second plate components 110, 112, the illustrated single force plate 102' also has an imaginary inner zone 154 that relates the area of the force plate to the controlled movement of the first and second game elements 122a, 122b.

While a subject is playing the interactive game by controlling the first and second game elements 122a, 122b by displacing his or her body on the surface(s) of the force measurement assembly 102, 102', the data acquisition/data processing device 104 is further configured to quantify the subject's performance while playing the interactive game using one or more game performance parameters (e.g., a numerical score). For example, a subject's performance while playing the interactive game may be quantitatively assessed using a running numerical score that is continually adjusted during the context of the game. In particular, an exemplary scoring technique may assign the subject a single numerical point every time he or she contacts the moving object (e.g., ball 124) with one of the movable game elements (e.g., paddles 122a, 122b), thereby changing the direction of travel of the object (e.g., the ball 124 is redirected towards the middle of the subject visual display device 106). Conversely, when the subject fails to contact the ball 124 with one of the paddles 122a, 122b, a single numerical point will be deducted from the subject's total score. For example, if a subject contacts the ball 124 a total of ten (10) times during the course of a game, but misses the ball 124 a total of three (3) times during the same game, he or she would be assigned a final numerical score of 7 (10 points minus 3 points equals a total score of 7) for the game.

As described above, some embodiments of the invention employ techniques that make the interactive game more challenging over time (e.g., the ball 124 travels at a faster speed across the screen or the size of the ball 124 is decreased over time). Thus, especially in these embodiments of the interactive game, it may be desirable to increase the amount of points that is assigned to the subject for successfully contacting the ball 124 with one of the paddles 122a, 122b for successive difficulty levels. For example, during a higher level of the game, when the ball 124 is moving faster across the screen and it has a smaller physical size (e.g., 124', 124", 124'"—see FIG. 4), a subject might be assigned 5 points for successfully contacting the ball 124 with the paddle, rather than the beginning point value of 1.

It is to be understood that above described scoring methodology is only one possible scoring technique that could be employed to quantitatively assess a subject's performance while playing the interactive game of the fall and/or concussion prediction system 100. As such, other alternative scoring techniques that quantitatively assess a subject's performance while playing the interactive game are also encompassed by the claimed invention.

The data acquisition/data processing device 104 is further configured to assess the probability that the subject will fall and/or predict whether or not the subject has sustained a concussion by using the one or more game performance parameters (e.g., the numerical score). In particular, the data acquisition/data processing device 104 may assess the probability that the subject tested will fall by relating the subject's final numerical score at the end of the game to a fall probability classification. For example, a final numerical score lying in the range from 0 to 10 points is equated with an indication of a "High Fall Probability" classification of the subject. A final numerical score lying in the range from 11 to 20 points is equated with an indication of a "Moderate Fall Probability" classification of the subject, and a final numerical score of 21 or greater points is equated with an indication of a "Low Fall Probability" classification of the subject. At the conclusion of the testing, the appropriate classification of the subject is outputted to the subject visual display device 106 so that the subject can be informed of his or her fall probability. The ranges for the exemplary fall classifications listed above initially are established by collecting normative data from one or more groups of experimental test subjects who have fallen. It is to be understood that these particular numerical ranges are presented for illustrative purposes only, and are in no way to be interpreted as limiting of the inventive scope.

In addition, the data acquisition/data processing device 104 may predict whether or not a subject has sustained a concussion by relating the subject's final numerical score at the end of a particular interactive game to one or more final numerical scores achieved by the same subject during one or more previous interactive games. For example, on day 1, prior to engaging in any athletic activities involving substantial contact with other players or another object (e.g., football or ice hockey), a first subject is tested several times using the fall and/or concussion prediction system 100, and receives an average numerical score of 25 (i.e., a baseline average numerical score) after playing 10 interactive games on the system. Subsequently, on day 30, after playing football, and sustaining a severe impact to the head during a tackle, the same subject is again tested on the fall and/or concussion prediction system 100. However, on day 30, the first subject only receives an average numerical score of 5 after playing 10 interactive games on the system. Based upon a comparison of the initial average score of 25 to the subsequent average score of 5, the fall and/or concussion prediction system 100 determines that the subject has "Possibly Sustained a Concussion". As another example, on day 1, prior to engaging in any athletic activities involving substantial contact with other players or another object, a second subject is tested several times using the fall and/or concussion prediction system 100, and receives an average numerical score of 18 (i.e., a baseline average numerical score) after playing 10 interactive games on the system. Subsequently, on day 45, after playing ice hockey, and sustaining a blow to the head from an opponent's hockey stick, the same subject is again tested on the fall and/or concussion prediction system 100. However, on day 45, the second subject receives an average numerical score of 17 after playing 10 interactive games on the system. Based upon a comparison of the initial average score of 18 to the subsequent average score of 17, the fall and/or concussion prediction system 100 determines that the subject "Does Not Readily Appear to Have Sustained a Concussion". In some instances, the data acquisition/data processing device 104 may also conclude that it is "Indeterminable Whether or Not Subject Has Sustained a Concussion" (e.g., when scores achieved by the subject are too erratic). As described above for fall prediction, at the conclusion of the testing, the predicted concussion evaluation of the subject is outputted to the subject visual display device 106 so that the subject can be informed of whether or not he or she has most likely sustained a concussion.

As will be appreciated by those skilled in the art, the one or more game performance parameters (e.g., numerical score(s)) that the data acquisition/data processing device 104 uses to quantify the subject's performance while playing the interactive game are indicative of the subject's balance, visual acuity, and reaction time. As individuals get older, their reaction time gets slower. Also, older individuals have decreased visual acuity and muscle strength. The interactive game described above is particularly well adapted to detect these factors of the subject. For example, when the size of the ball 124 is decreased during the subsequent levels of the game, an older individual may reach a point when he or she is no longer able to see the ball 124. Moreover, even if an older individual is able to see the ball 124, he or she may not be able to react quickly enough to contact the ball 124 with one of the paddles 122a, 122b because he or she has a slow reaction time. Furthermore, even if an individual is able to see the ball 124 and can react quickly enough, the subject may lose his or her balance when he or she is attempting to move in response to the moving ball 124.

In one or more embodiments, the fall and/or concussion prediction system 100 is used to determine a subject's point of failure during the interactive game, the virtual reality scenario or the immersive graphic environment. For example, during the exemplary interactive game described above, it may be determined that the subject fails to see the ball once its speed exceeds a certain predetermined threshold. The subject's inability to see the ball may be indicative of a deficiency in the subject's visual acuity. Alternatively, if the subject has a cognitive disorder, the subject may be unable to understand the movement of the ball during the interactive game. Advantageously, once the subject's deficiency is identified, the appropriate corrective measures can be taken (e.g., measures can be taken to strengthen the subject's vision).

Figure 19:
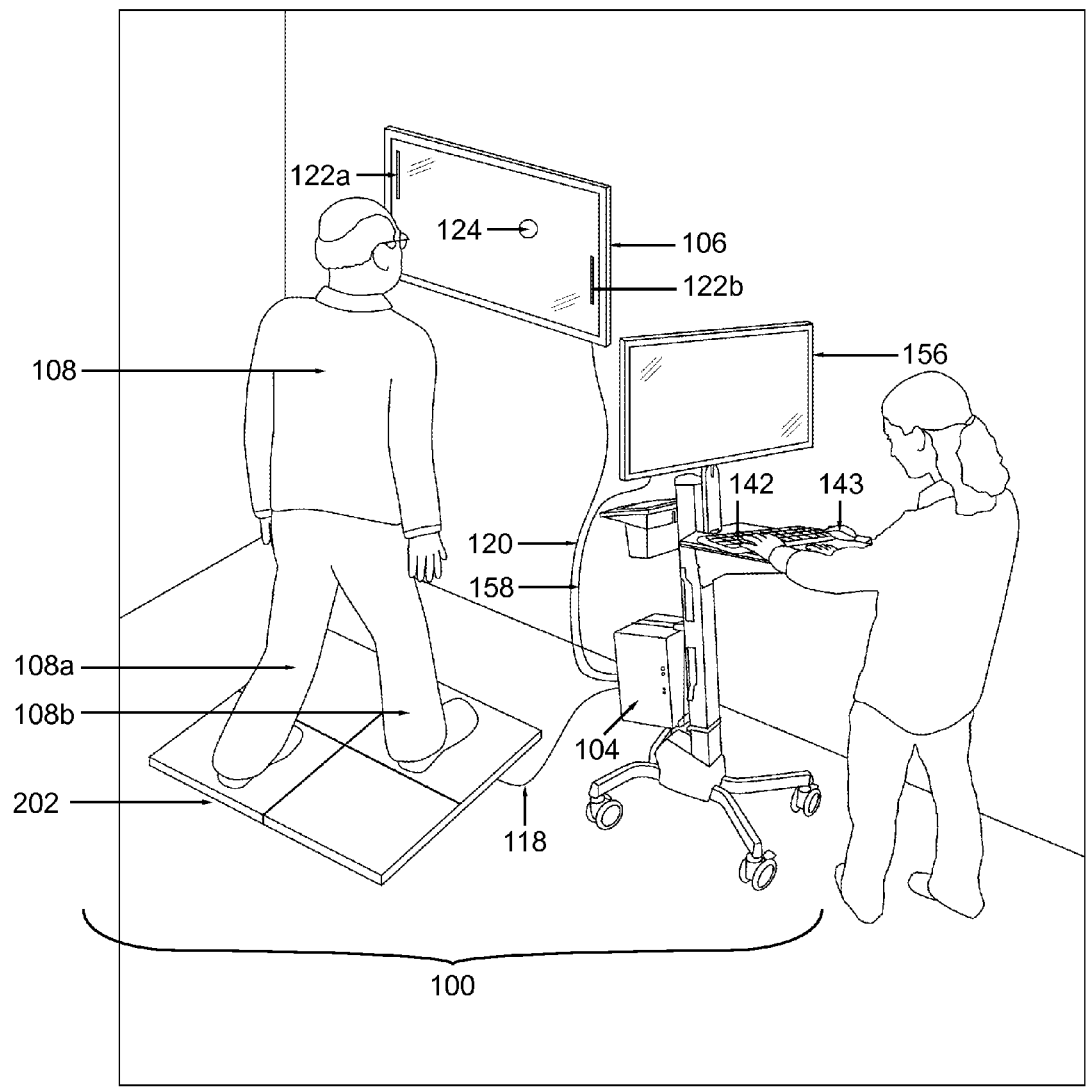
FIG. 19 is a diagrammatic perspective view of a system for fall and/or concussion prediction according to an alternative embodiment of the invention, wherein an interactive game is being displayed on the subject visual display device and the measurement device is in the form of a contact or timing mat having four quadrants.

An alternative embodiment of the fall and/or concussion prediction system 100 is illustrated in FIG. 19. In this embodiment, a contact or timing mat 202 having four quadrants is provided in lieu of the force measurement assembly 102. The movement of each paddle 122a, 122b is controlled in this embodiment based upon the movement of the subject's feet into the particular quadrants of the contact mat 202. For example, if the subject 108 wishes to move the paddle 122a in an upward direction on the visual display device 106, he or she moves his left foot/leg 108a from the left-rear quadrant of the contact mat 202 to the left-front quadrant of the mat 202. Similarly, if the subject 108 wishes to move the paddle 122b in a downward direction on the visual display device 106, he or she moves his right foot/leg 108b from the right-front quadrant of the contact mat 202 to the right-rear quadrant of the mat 202. In this manner, the subject 108 is able to shift the paddles 122a, 122b up or down on the screen by selectively positioning his or her feet in the appropriate quadrant on the contact mat 202.

In one or more further embodiments of the invention, the fall and/or concussion prediction system 100 utilizes a dual-task protocol to assess a person's risk for falling and/or predict whether or not a person has sustained a concussion. The first task of the dual-task protocol may comprise a cognitive task (i.e. a task which requires a particular mental process), while the second task of the dual-task protocol may comprise a motor or muscular task (i.e. a task which requires the use of muscles of the body). In one or more embodiments, the first cognitive task is performed concurrently with the second motor task so that a subject has to perform both tasks simultaneously.

The first cognitive task may comprise a variety of different cognitive tasks. For example, the cognitive task could require the subject to recite the alphabet forward or backward, recite a series of numbers forward or backward, perform mathematical computations, count auditory tones, spell words, identify colors, answer a series of questions, or repeat a series of letters or numbers, etc. In particular, the performance of mathematical computations could comprise performing serial-3 subtraction (e.g., starting with 30, subtract 3 from 30, subtract 3 from 27, and then keep subtracting 3 from the resulting number as many times as possible), performing serial-7 subtraction (e.g., starting with 100, subtract 7 from 100, subtract 7 from 93, and then keep subtracting 7 from the resulting number as many times as possible), adding, subtracting, or multiplying any selected numbers, or performing different types of currency calculations (e.g., if an item costs $1.58 and you give the cashier $2.00, how much change do you get back?). One of ordinary skill in the art will readily appreciate that these are merely exemplary cognitive tasks, and that other suitable cognitive tasks may be employed in conjunction with the claimed invention.

Figure 11:
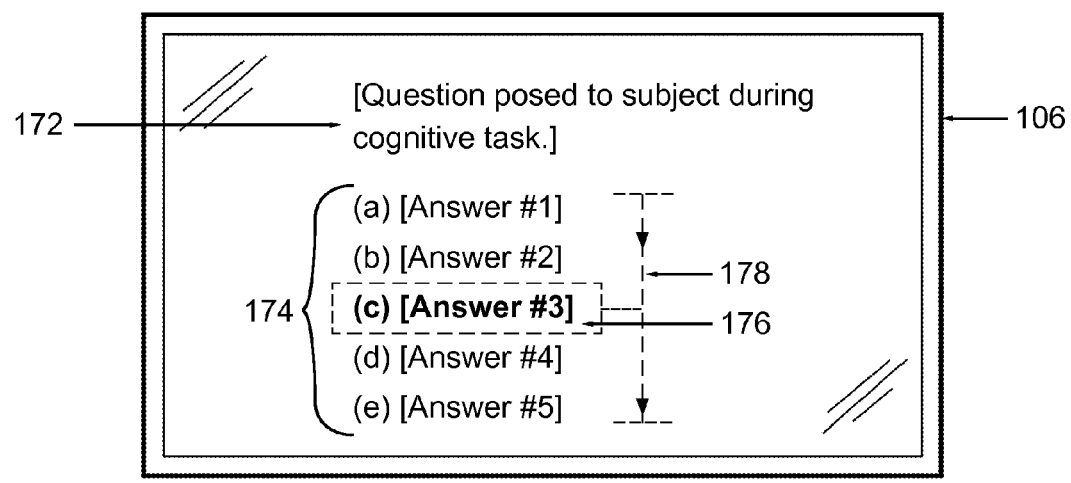
FIG. 11 is a diagrammatic frontal view of the subject visual display device of the fall and/or concussion prediction system with a first exemplary cognitive task displayed thereon, wherein the question and the answer choices are displayed simultaneously on the screen, according to an embodiment of the invention.
Figure 12:
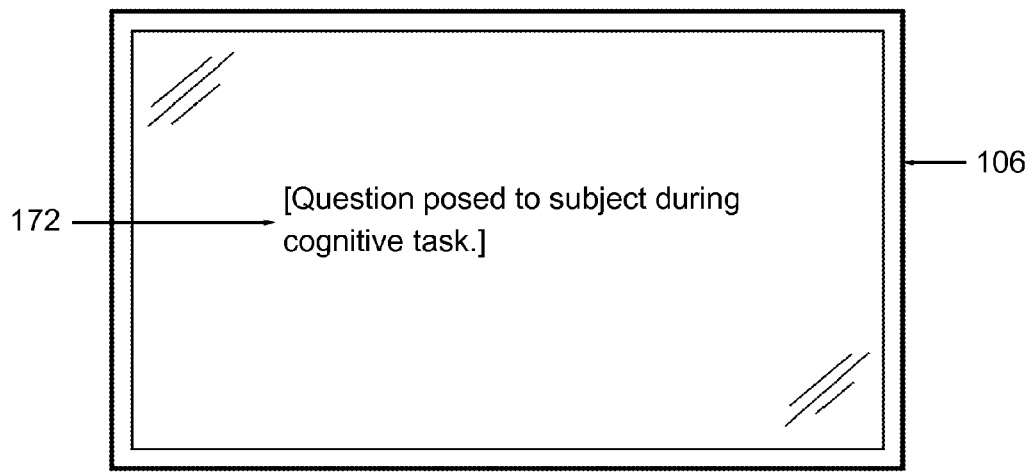
FIG. 12 is a diagrammatic frontal view of the subject visual display device of the fall and/or concussion prediction system with a first exemplary cognitive task displayed thereon, wherein only the question is displayed on the screen, according to an embodiment of the invention.
Figure 13:
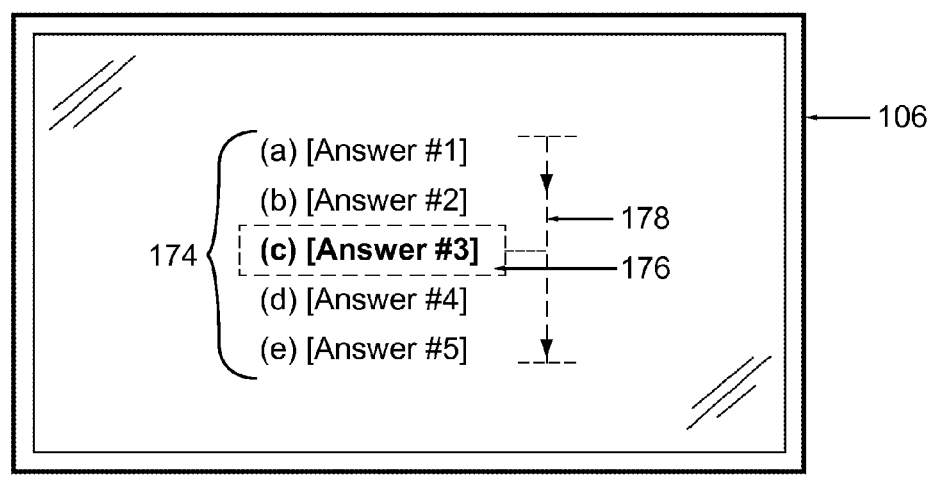
FIG. 13 is a diagrammatic frontal view of the subject visual display device of the fall and/or concussion prediction system with a first exemplary cognitive task displayed thereon, wherein only the answer choices are displayed on the screen, according to an embodiment of the invention.

In a preferred embodiment, the first cognitive task is in the form of a multiple choice test (as shown in FIGS. 10-13), and the right and wrong answers 174 are displayed on the subject visual display device 106 in list form (refer to FIGS. 11 and 13). The subject is able to select the answer that he or she believes is correct by using a selection device or clicker 168 (see FIG. 10). The selection device or clicker 168 is operatively coupled to the data acquisition/data processing device 104 by means of a data transmission cable 170. In one embodiment, the clicker or selection device 168 contains a single pushbutton that is depressed by the subject. When a clicker 168 having a single pushbutton is used, the answers 174 to the multiple choice questions (e.g., question 172 in FIGS. 11 and 12) are highlighted one at a time in sequence (as indicated by diagrammatic dashed lines 178 in FIGS. 11 and 13), and the subject pushes the single pushbutton at the appropriate time to select the correct answer (e.g., the bold answer 176 in FIGS. 11 and 13). In another embodiment, the clicker or selection device 168 comprises up/down arrow button(s) and a selector button. When a clicker having this configuration is used, the subject uses the up/down arrow button(s) to navigate to the correct answer in the list of answers 174, and then uses the selector to choose the correct answer (e.g., the bold answer 176 in FIGS. 11 and 13). In FIGS. 11-13, the text associated with the questions and answers 172, 174 is included in brackets in order to represent that any suitable question for a cognitive task with any suitable set of answers may be displayed on the subject visual display device 106.

Figure 14:
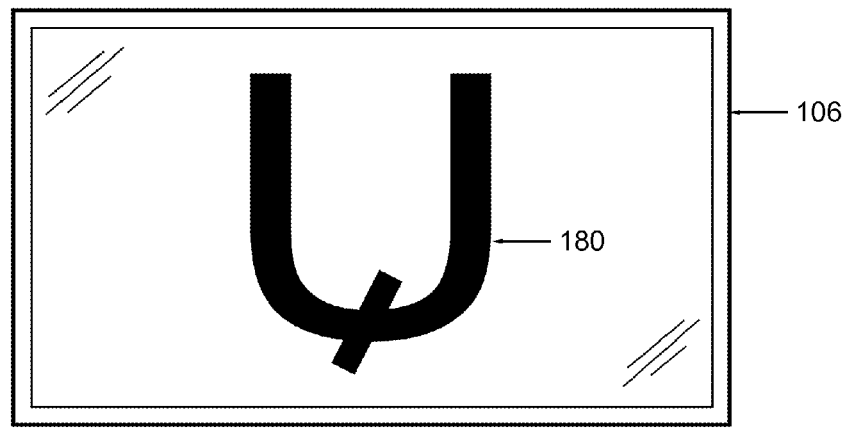
FIG. 14 is a diagrammatic frontal view of the subject visual display device of the fall and/or concussion prediction system with a second exemplary cognitive task displayed thereon, wherein a symbol that the subject is to match is depicted on the screen, according to an embodiment of the invention.
Figure 15:
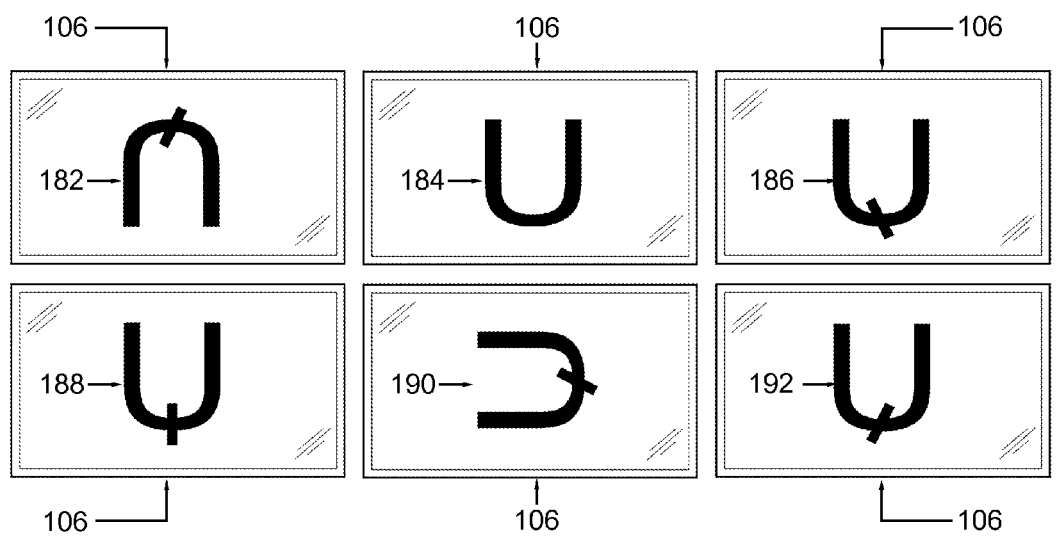
FIG. 15 illustrates diagrammatic frontal views of a plurality of subject visual display devices of the fall and/or concussion prediction system with various symbol choices for a second exemplary cognitive task displayed thereon, according to an embodiment of the invention.

In another preferred embodiment, a letter, number, and/or symbol, or a pattern of letters, numbers, and/or symbols, is displayed on the subject visual display device 106, and the subject uses the selection device or clicker 168 when a letter, number, or symbol that matches the initially presented letter, number, and/or symbol, or fits the initially presented pattern, appears on the screen. For example, as shown in FIG. 14, a symbol 180 is initially displayed on the subject visual display device 106. Then, the subject is instructed to indicate when a matching symbol subsequently appears on the subject visual display device 106 by depressing the pushbutton on the selection device or clicker 168. As shown in FIG. 15, after the initial symbol is displayed, a series of subsequent symbols 182-192 are displayed sequentially on the subject visual display device 106. Finally, when a symbol matching the initial symbol 180 is displayed on the subject visual display device 106, the subject depresses the pushbutton on the selection device or clicker 168 to indicate that he or she has identified a matching symbol (e.g., matching symbol 192 in FIG. 15).

Similarly, the second motor task may comprise a variety of different motor or muscular tasks, which are performed on the surface(s) of the force measurement assembly 102 (e.g., a force plate or instrumented treadmill). For example, the motor or muscular task could require the subject to remain as stationary as possible on the force measurement surface(s), walk a predetermined distance on the force measurement surface(s), run a predetermined distance on the force measurement surface(s) (e.g., on an instrumented treadmill surface), perform a toe-to-heel tandem walking exercise on the force measurement surface(s), perform a step quick turn exercise on the force measurement surface(s), perform a forward lunge exercise on the force measurement surface(s), maintain his or her balance on a moving force measurement surface (e.g., on a dynamic force plate), balance one or more objects while disposed on the force measurement surface(s) (e.g., carrying and balancing a tray with empty cups or cups filled with water disposed thereon), move from a standing position to a seated position while disposed on the force measurement surface(s), move from a seated position to a standing position while disposed on the force measurement surface(s), step up and over an obstruction (i.e., obstacle, such as a box) while disposed on the force measurement surface(s), or step up and on obstacle then back down while disposed on the force measurement surface(s). Similar to that which was described above for the cognitive tasks, one of ordinary skill in the art will readily appreciate that these are merely exemplary motor tasks, and that other suitable motor tasks may be employed in conjunction with the claimed invention.

In addition, it is to be understood that various performance assessment parameters could be used to assess a subject's performance during the execution of the motor or muscular tasks set forth above. For example, when the subject is instructed to move from a seated position to a standing position, the force measurement assembly 102 could be used to compute: (a) weight transfer time, (b) rising index, (c) center of gravity COG sway velocity, and (d) left/right weight symmetry (an average or mean for each of these parameters can also be computed). When the subject is instructed to walk a predetermined distance across the force measurement surface(s), the data acquired from the force measurement assembly 102 could be used to compute: (a) step width, (b) step length, (c) gait speed, and (d) step length symmetry. During the performance of a toe-to-heel tandem walking exercise by the subject, the data acquired from the force measurement assembly 102 could be used to compute: (a) step width, (b) gait speed, and (c) anterior-posterior (A/P) COG sway velocity. When the subject is instructed to perform a step quick turn exercise on the force measurement surface(s), the data acquired from the force measurement assembly 102 could be used to compute: (a) turn time, (b) turn time difference, (c) turn sway, and (d) turn sway difference. When the subject is instructed to step up and over an obstruction, the data acquired from the force measurement assembly 102 could be used to compute: (a) lift-up index, (b) lift-up index difference, (c) movement time, (d) movement time difference, (e) impact index, and (f) impact index difference. During the performance of a forward lunge exercise on the force measurement surface(s), the data acquired from the force measurement assembly 102 could be used to compute: (a) length of the forward step, (b) distance measured between the right and left legs, (c) impact index, (d) impact index difference, (e) contact time difference, (f) force impulse, and (g) force impulse difference. When the subject is instructed to carry and balance a tray with empty cups or cups filled while disposed on the force measurement surface(s), the data acquired from the force measurement assembly 102 could be used to compute: (a) a center of pressure (COP) tracing, and/or (b) a center of gravity (COG) tracing for the subject 108. Other possible performance parameters that could be computed using the data acquired from the force measurement assembly 102 include, but are not limited to: (a) COG Sway Velocity, (b) Mean COG Sway Velocity, (c) COG Alignment, (d) Reaction Time, (e) Movement Velocity (MVL), average speed of COG movement, expressed in degrees per second, (f) Endpoint Excursion (EPE), (g) Maximum Excursion (MXE), (h) Directional Control (DCL), (i) On-Axis Velocity, (j) COP Sway Range, and (k) COP Sway Velocity. Also, it is to be understood that an average or mean for each of the above described parameters could also be computed (e.g., by computing an average value for parameters acquired during the performance of a series of trials).

Initially, at the beginning of the dual-task protocol, the subject is positioned on the force measurement assembly (102, 102a/102b, 102', 102"). If the dual force plate assembly 102 is utilized for the dual-task protocol, the feet of the subject 108 will be placed on respective first and second measurement surfaces 114, 116. In contrast, if the single force plate 102' is used for the dual-task protocol, both feet of the subject will be placed on the single measurement surface of the force plate 102'. Next, a scene will be displayed on the subject visual display device 106 that relates to the performance of the first cognitive task. For example, if the cognitive task involves a series of multiple choice questions, the subject may be presented with a list of answers to each question on the subject visual display device 106. Then, the subject will be instructed to perform the second motor task. After performing the motor task, the clinician then will instruct the subject to perform the first cognitive task in conjunction with the second motor task, which comprises one or more movements on the surface or surfaces of the force measurement assembly 102. Advantageously, during the execution of the dual task protocol by the subject, the force measurement assembly 102 is used to: (i) verify that the motor task is actually being performed by the subject (i.e., to verify that the subject is not just focusing on the cognitive task and skipping the motor task and/or (ii) determine the subject's performance of the motor task. In other words, during the dual task protocol, the force measurement assembly 102 is used in an analytical manner. While the subject performs the motor task, the force transducers of the force measurement assembly 102 are used to sense the forces and/or moments that are applied to the surface of the force measurement assembly 102 by the subject. The signals from the force transducers of the force measurement assembly 102 are transmitted to the data acquisition/data processing device 104, and the data acquisition/data processing device 104 computes one or more numerical values (e.g., the subject's center of pressure or center of gravity) from the signals. For example, if the force measurement assembly 102 is being used to verify that the motor task is actually being performed by the subject, the variation or change in the subject's center of pressure could be evaluated. If the center of pressure of the subject remains virtually unchanged (e.g., it does not exceed a certain predetermined threshold) during the simultaneous performance of the cognitive and motor tasks, this may indicate that the subject is not performing the motor task at all. For example, suppose the subject is asked to perform a step up/step over motor task, if the y coordinate of the center of pressure does not exceed a predetermined value (e.g., y=2) during the performance of the motor task, then the clinician may conclude that the subject is not performing the motor task, and is just focusing on the cognitive task.

In one or more embodiments, the force measurement assembly 102 is in the form of a static force plate (i.e., the force plate surface is stationary and is not displaced relative to the floor or ground). Such a static force plate does not have any actuators or other devices that translate or rotate the force measurement surface. In one or more alternative embodiments, the force measurement assembly 102 is in the form of a dynamic force plate (i.e., the force plate surface is displaced and/or translated relative to the floor or ground). As such, a dynamic force plate contains one or more actuators or other devices that are capable of translating and/or rotating the force plate surface.

In the one or more embodiments, the data acquisition/data processing device 104 converts the computed center of pressure (COP), as described above, to a center of gravity (COG) for the subject using a Butterworth filter. For example, in one exemplary, non-limiting embodiment, a second-order Butterworth filter with a 0.75 Hz cutoff frequency is used. In addition, the data acquisition/data processing device 104 also computes a sway angle for the subject using a corrected center of gravity (COG') value, wherein the center of gravity (COG) value is corrected to accommodate for the offset position of the subject relative to the origin of the coordinate axes (130, 132, 134, 136) of the force measurement assembly 102. For example, the data acquisition/data processing device 104 computes the sway angle for the subject in the following manner:

$$\theta = \sin^{-1}\left(\frac{COG'}{0.55h}\right) - 2.3° \tag{9}$$

where:
θ: sway angle of the subject;
COG': corrected center of gravity of the subject; and
h: height of the center of gravity of the subject.

The data acquisition/data processing device 104 is used to quantitatively determine a subject's performance during the first and second tasks. The assessment of the subject's performance of the second motor task is based at least partially upon the one or more numerical values computed from the signals of the force measurement assembly 102. The subject's performance of the first cognitive task is quantitatively expressed in terms of one or more first performance values, while the subject's performance of the second task is quantitatively expressed in terms of one or more second performance values.

Figure 9:
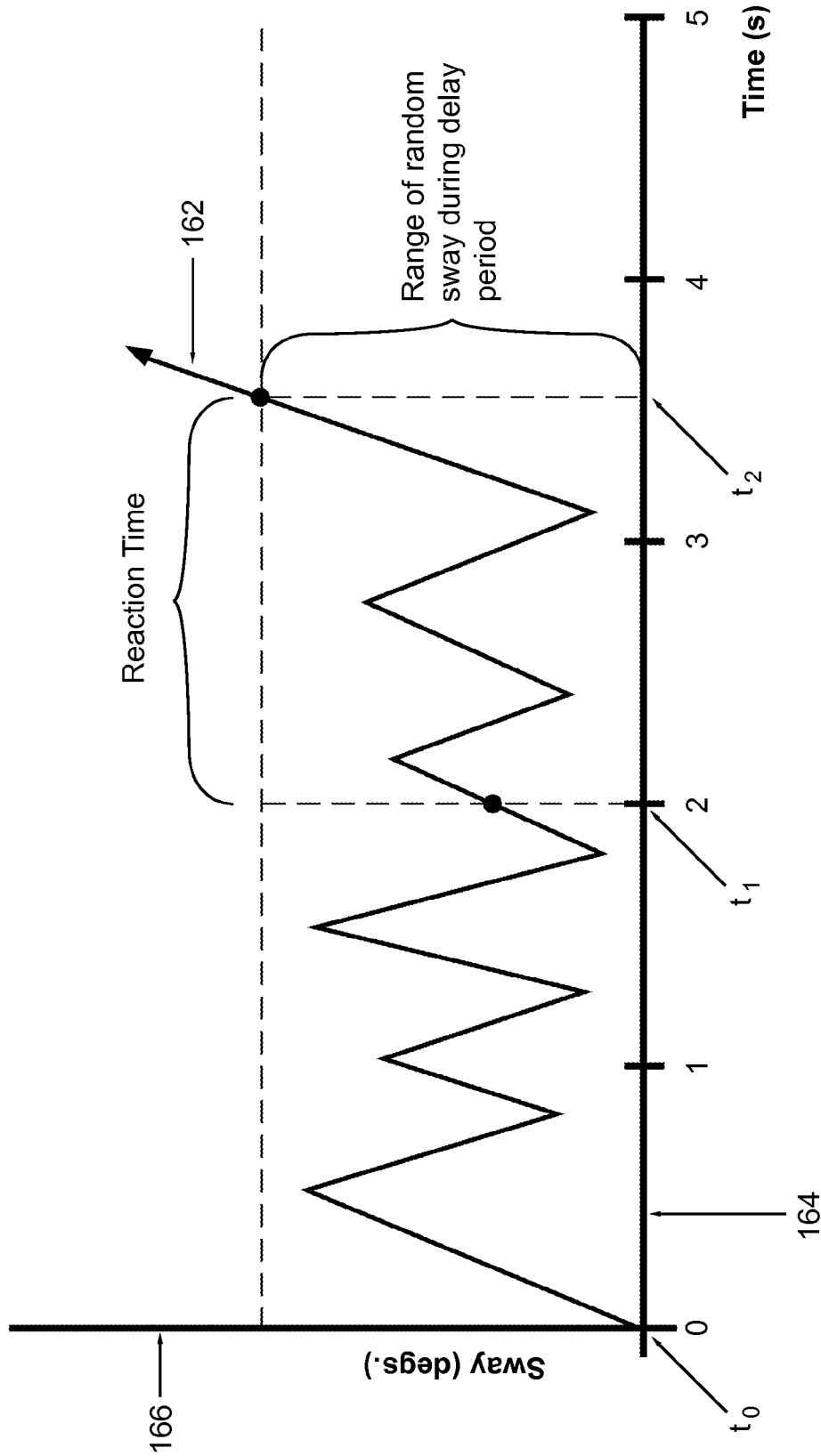
FIG. 9 is a graphical depiction illustrating an exemplary manner in which the reaction time is calculated for a subject during the performance of a motor or muscular task.
Figure 10:
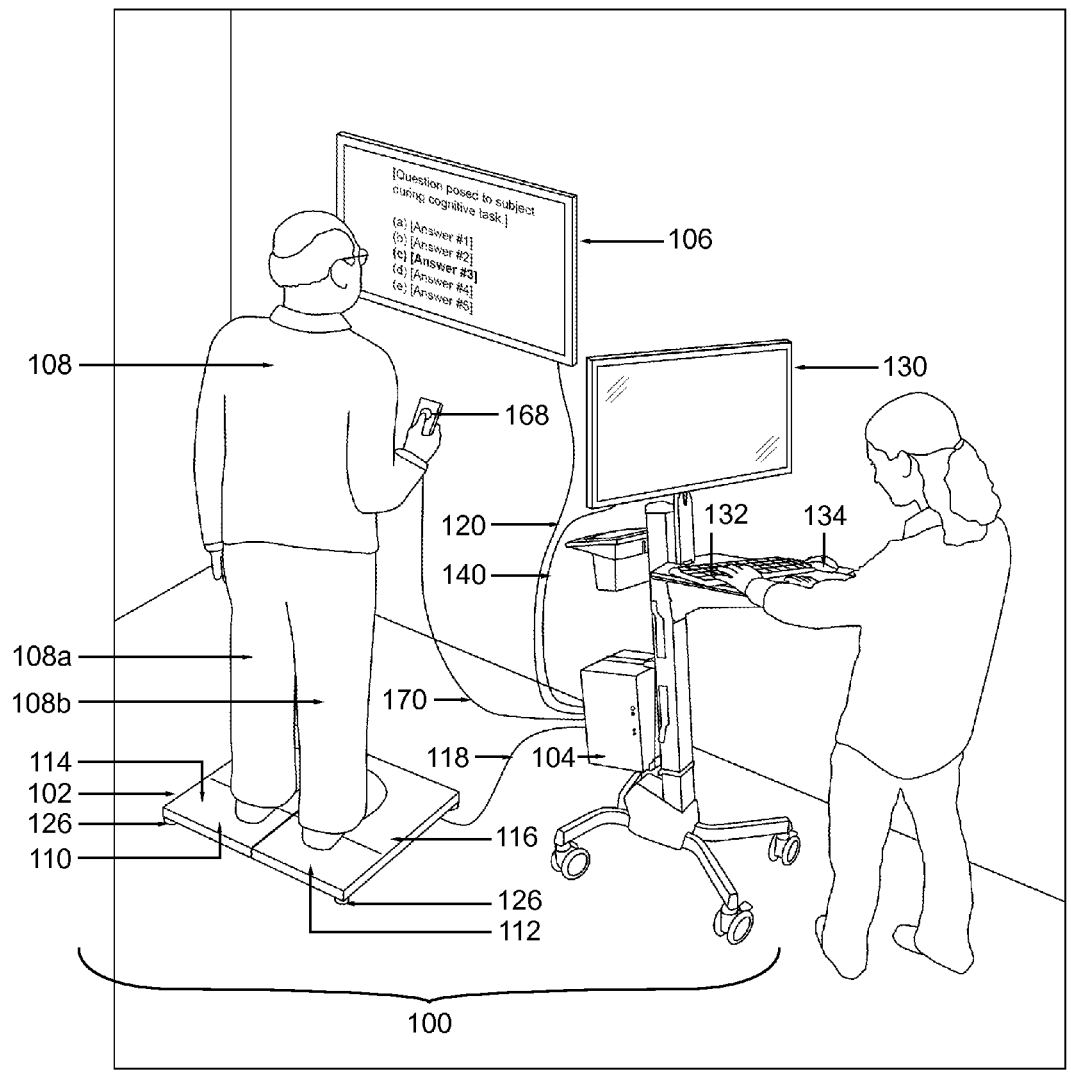
FIG. 10 is a diagrammatic perspective view of a system for fall and/or concussion prediction according to an embodiment of the invention, wherein a cognitive task of a dual task protocol is being displayed on the subject visual display device.

Finally, the probability that the subject will fall and/or the prediction of whether or not a subject has sustained a concussion is determined by using at least one of the one or more first and second performance values (i.e., one or more numerical scores). In one or more embodiments, a slow down in the subject's performance during the first cognitive task (i.e., decreased mental ability) and/or a slow down in the subject's performance during the second motor task (i.e., decreased physical ability) may be used to predict if a subject will fall and/or predict whether or not a subject has sustained a concussion. A slow down in the subject's performance during the first and second tasks may be determined by measuring the subject's reaction time (RT) during the performance of the cognitive and motor tasks. For example, during the performance of a cognitive task, the reaction time (RT) is the duration of time (e.g., measured in seconds) between the time when a question is posed to the subject (e.g., when a question is displayed on the subject visual display device 106) and the subject's actual answering of the question (e.g., by indicating his or her response using the clicker device 168). Similarly, during the performance of a motor task, the reaction time (RT) is the duration of time (e.g., measured in seconds) between the time when the subject is given a signal or cue to move (e.g., by displaying a visual indicator on the subject visual display device 106) and the subject's actual initiation of movement. The data acquisition/data processing device 104 computes the reaction time of the subject and determines the start of intentional subject movement towards a particular target. For example, referring to FIG. 9, at time $t_0$ (t=0), the operator depresses a key on the keyboard 142 of the computing device 104 to initiate the beginning of a predetermined time delay (e.g., a time delay of 2 seconds). At the end of the predetermined time delay ($t_1$=2 seconds), the subject is given a signal or cue to move (e.g., a cue is displayed on the subject visual display device 106). Then, at time $t_2$, it is determined that the subject's sway (indicated by sway signal 162 in FIG. 9) exceeds the random range (e.g., $t_2$=3.60 seconds). As such, in this example, the subject's reaction time (RT) is $t_2$-$t_1$=3.60 seconds minus 2.00 seconds=1.60 seconds. Typically, during the performance of the motor test or task, the subject will be asked to move as quickly as possible. Consequently, a small value for the reaction time is desirable, while a large value for the reaction time is undesirable. In addition, other suitable parameters may be used to assess the subject's performance during the performance of the motor task. For example, the center of pressure (COP) sway range or the center of gravity (COG) sway range could also be used for assessing performance. Moreover, the COP sway velocity (measured in centimeters per second or inches per second) or the COG sway velocity (measured in degrees per second) also could be utilized to assess the performance of the subject during certain motor tests or tasks. For the cognitive test or task, the accuracy with which the subject answers the questions (i.e., how many questions he or she gets right) also may be used in conjunction with the reaction time in order to assess the subject's overall performance thereof.

In one or more embodiments of the invention, a series of tests are performed in conjunction with the dual-task protocol. For example, in one such variation, the subject initially will be asked to perform a cognitive task (e.g., answering a series of multiple choice questions that are posted on the subject visual display device 106). Next, the subject will be instructed to perform a motor/muscular task (e.g., stepping up and over an obstacle disposed on the surface of the force measurement assembly 102). Finally, the subject will be asked to perform both the cognitive task and the motor/muscular task simultaneously (i.e., the performance of dual tasks). Moreover, the results during each of the tests can also be compared to the results from a baseline test (i.e., results generated during tests that were performed before the subject had fallen or sustained a concussion, when the subject was considered healthy).

Now, an exemplary dual-task protocol carried out by the fall and/or concussion prediction system 100 will be described in detail. Initially, the subject is instructed to perform a cognitive task. For example, suppose the subject is asked to perform the symbol-based cognitive task illustrated in FIGS. 14 and 15. As described above, the symbol 180 (which is required to be matched by the subject) is initially displayed on the subject visual display device 106. Referring again to FIG. 15, a series of symbols 182-190, which are intended to resemble the symbol 180, are displayed on the subject visual display device 106 in succession. One or more of these symbols 182-190 are intended to very closely resemble the initial symbol 180 so as to challenge the subject's cognitive abilities. For example, symbol 186 in FIG. 15 very closely resembles symbol 180 in FIG. 14 (i.e., the only difference between the two symbols 180, 186 is the orientation of the diagonal line disposed across the bottom leg of the U-shaped symbol). When a symbol (e.g., symbol 192) is displayed on the subject visual display device 106 that exactly matches the initial symbol 180, the subject makes his or her selection by depressing the pushbutton on the selection device or clicker 168. During the cognitive task, this same process is repeated for a plurality of different symbols. Preferably, the geometry of each of these symbols will differ significantly from one another so as to accurately test the subject's cognitive ability. In addition, a series of cognitive tasks are preferably performed so that an average for a plurality of cognitive tasks can be computed. During the execution of each cognitive task, the accuracy and reaction time of the subject's performance will be automatically computed by the data acquisition/data processing device 104. In order to determine the subject's accuracy during each cognitive task/test, the data acquisition/data processing device 104 will keep track of the number of questions that the subject answers correctly (e.g., the quantity of symbols that were correctly matched by the subject). In addition, the data acquisition/data processing device 104 will also compute the subject's reaction time in answering each question during the cognitive task/test. In one or more embodiments, the reaction time will be determined by the data acquisition/data processing device 104 by computing the difference between the time ($t_2$) the question is answered by the subject (i.e., when he or she depresses the pushbutton on the clicker 168) and the time ($t_1$) when the question is first posed to the subject (i.e., when the symbol is first displayed on the subject visual display device 106). In other words, the reaction time is equal to time $t_2$ minus time $t_1$ (e.g., $t_2$-$t_1$=15 seconds=0 seconds=15 second reaction time).

After the subject completes the initial cognitive task(s), the subject then performs a motor/muscular task(s) on the surface of the force measurement assembly (102, 102a/102b, 102', 102"). In an exemplary embodiment, the motor/muscular task comprises a step up/step down protocol (refer to FIGS. 16A-16C and 17A-17C). Initially, at the beginning of the step up/step down protocol (e.g., see FIG. 16A), the subject steps up onto an obstacle (i.e., a curb or box 194) with one of his or her legs (e.g., the right leg 108b). Then, the subject 108 lifts his or her other leg (e.g., the left leg 108a, which is the lagging or trailing leg) onto the curb or box 194 such that both legs/feet 108a, 108b are positioned on the top of the box 194 (as shown in FIG. 16B). Finally, the subject 108 the steps backward off the box 194, and back onto the surface of the force measurement assembly 102a. For example, the subject 108 initiates his backward movement by first moving his or right leg 108b back to the surface of the force measurement assembly 102a (see FIG. 16C). Then, the subject brings his or her other leg (e.g., the left leg/foot 108a) down from the box 194 and places it onto the surface of the force measurement assembly 102a next to the right foot. In one or more embodiments, this first routine of the task is repeated for a plurality of trials (e.g., two or three trials). Then, the subject switches the roles of his or her feet in the step up/step down protocol and performs a second set of trials. In the second set of trials, the subject initially steps up onto an obstacle (i.e., a curb or box 194) with the opposite leg as compared to that used in the first set of trials (e.g., the left leg/foot 108a). Then, the subject 108 lifts his or her other leg (e.g., the right leg 108b) onto the curb or box 194 such that both legs/feet 108a, 108b are positioned on the top of the box 194. Finally, the subject 108 the steps backward off the box 194, and back onto the surface of the force measurement assembly 102a. In the second set of trials, the subject 108 initiates his backward movement by first moving his or left leg 108a back to the surface of the force measurement assembly 102a (opposite to that which was described for the first set of trials). As described above for the first routine, this second routine can also be repeated for a plurality of trials (e.g., two or three trials).

Figure 16A:
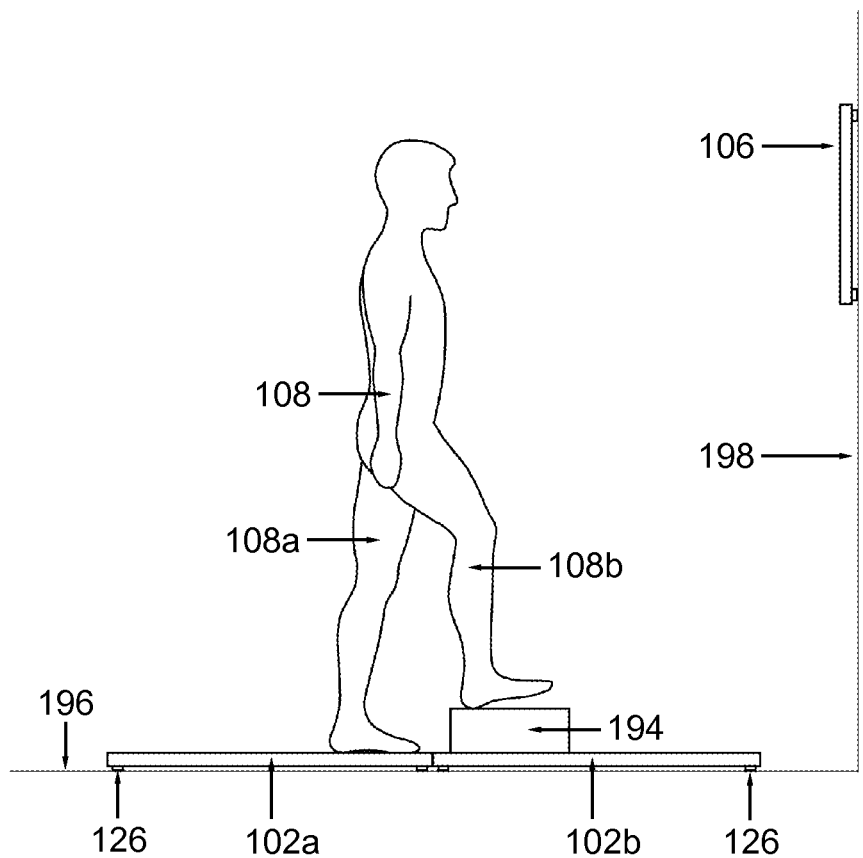
FIG. 16A diagrammatically illustrates a subject performing a first stage of an exemplary motor or muscular task on the surface of a first force measurement assembly, wherein the obstacle or box is disposed on the surface of the first force measurement assembly, according to an embodiment of the invention.
Figure 16B:
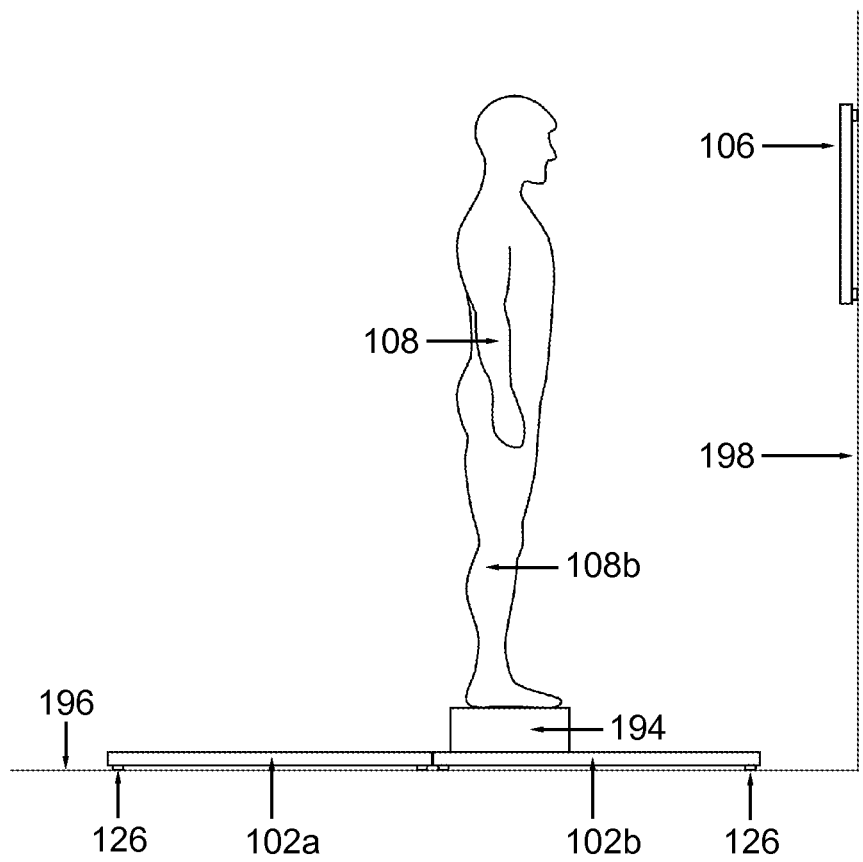
FIG. 16B diagrammatically illustrates a subject performing a second stage of an exemplary motor or muscular task on the surface of a first force measurement assembly, wherein the obstacle or box is disposed on the surface of the first force measurement assembly, according to an embodiment of the invention.
Figure 16C:
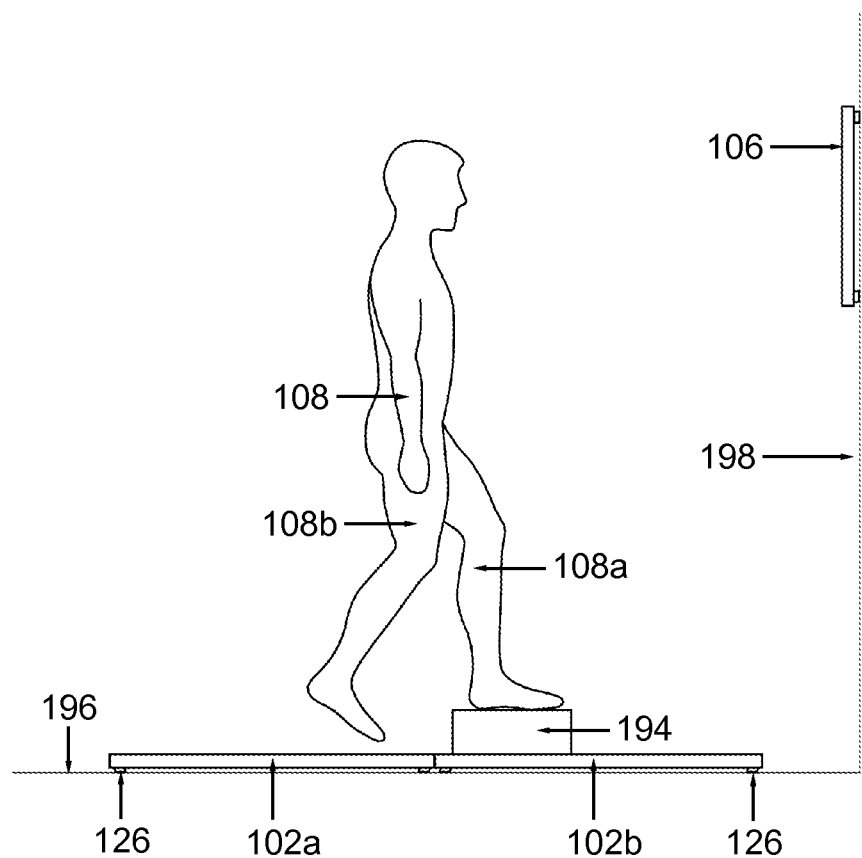
FIG. 16C diagrammatically illustrates a subject performing a third stage of an exemplary motor or muscular task on the surface of a first force measurement assembly, wherein the obstacle or box is disposed on the surface of the first force measurement assembly, according to an embodiment of the invention.

As illustrated in FIGS. 16A-16C, when the box 194 is positioned on the surface of the force measurement assembly, two (2) force measurement assembly modules 102a, 102b may be provided in order to increase the overall force plate surface area. Advantageously, the increased surface area provided by two force measurement assembly modules 102a, 102b (or force plate modules 102a, 102b) provides the subject with additional room with which to safely perform the motor or muscular task (e.g., step up/step down protocol).

In addition, in an alternative embodiment, a pressure mat or timing device (e.g., a contact mat with time measurement capabilities) is used in lieu of the force measurement assembly 102 or force measurement assembly modules 102a, 102b. For example, with reference to FIG. 16A, each of the force measurement assembly modules 102a, 102b could each be replaced with a pressure mat or contact mat. Pressure mats could be used to output the subject's foot pressure distribution and/or force and pressure time integrals computed using the subject's foot pressure distribution. Contact mats, if substituted for each of the force measurement assembly modules 102a, 102b, could be used to output the time duration between the subject's successive contact periods with the mat surface. As such, the rhythm and timing of the subject could be determined during the performance of the motor task so that it could be determined whether or not the motor task was being properly performed by the subject. For example, if the subject failed to perform the rhythmic motion of stepping up and down on and off the box 194 for a certain period of time during the performance of the motor task, one of the contact mats would measure a longer time duration between contact peaks with its respective surface.

Figure 17A:
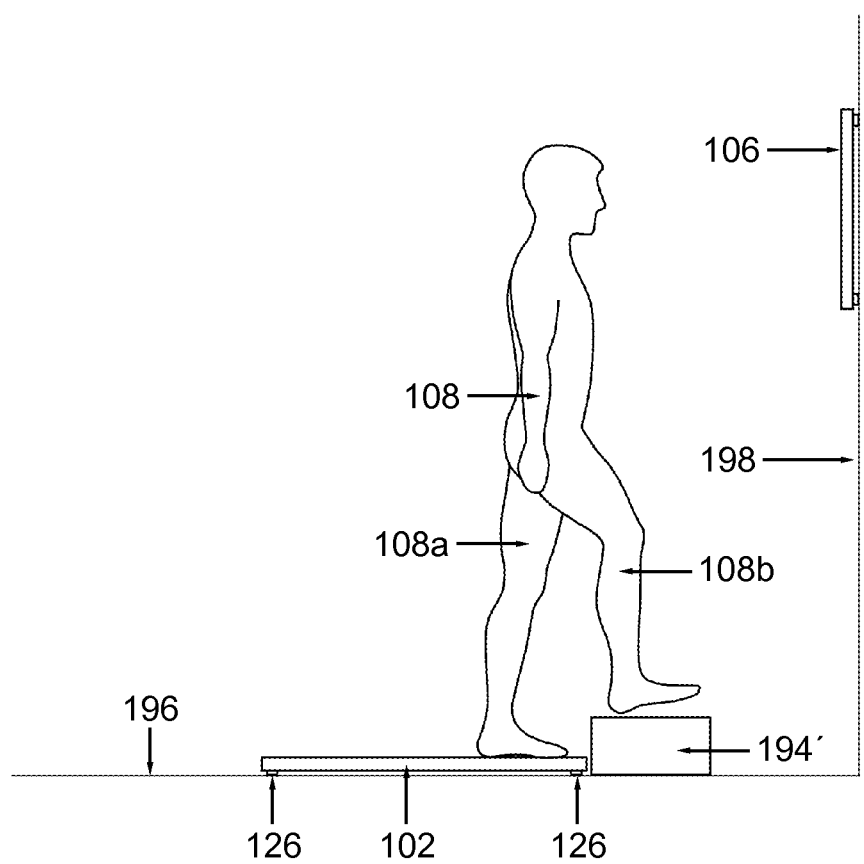
FIG. 17A diagrammatically illustrates a subject performing a first stage of an exemplary motor or muscular task on the surface of a second force measurement assembly, wherein the obstacle or box is disposed on a floor, according to an embodiment of the invention.
Figure 17B:
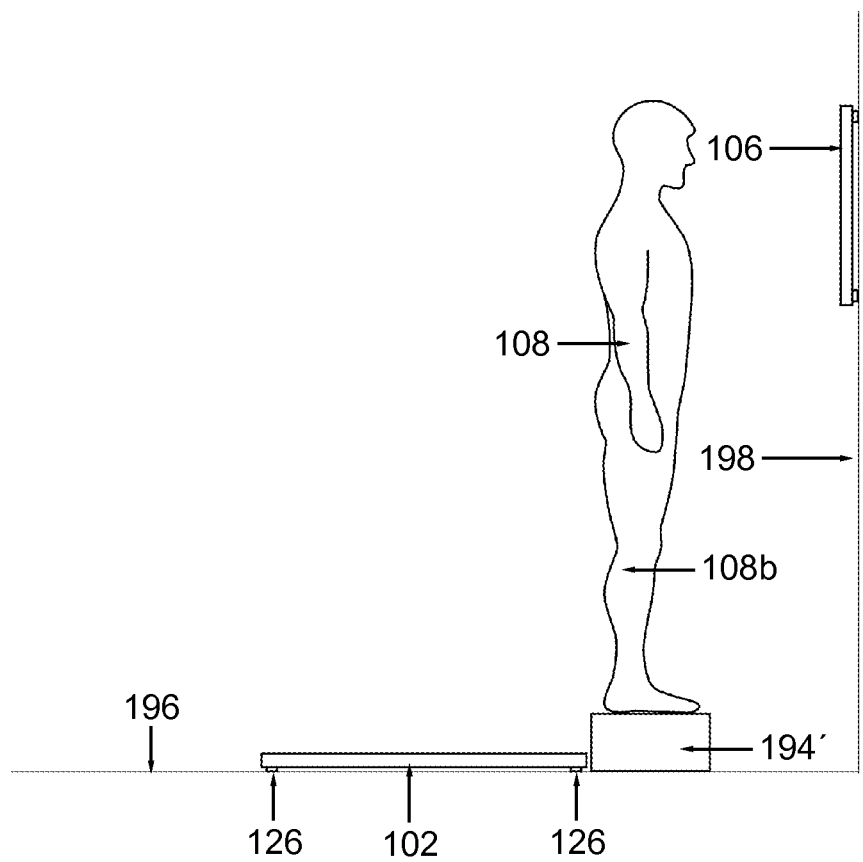
FIG. 17B diagrammatically illustrates a subject performing a second stage of an exemplary motor or muscular task on the surface of a second force measurement assembly, wherein the obstacle or box is disposed on the floor, according to an embodiment of the invention.
Figure 17C:
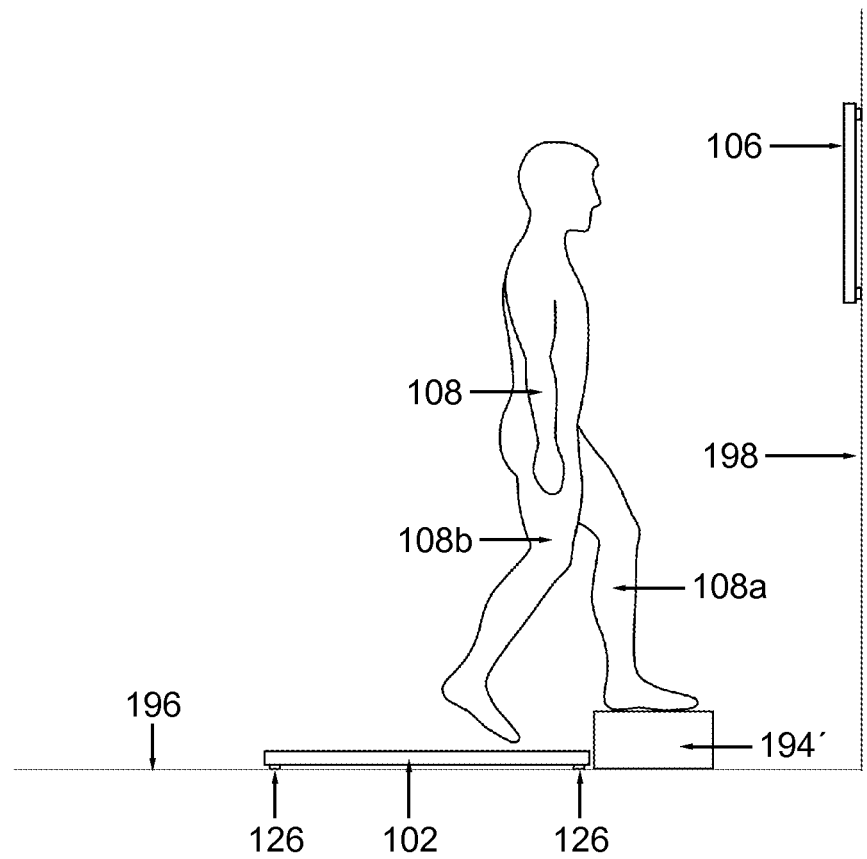
FIG. 17C diagrammatically illustrates a subject performing a third stage of an exemplary motor or muscular task on the surface of a second force measurement assembly, wherein the obstacle or box is disposed on the floor, according to an embodiment of the invention.

A variation of the step up/step down protocol is illustrated in FIGS. 17A-17C. In these figures, the step up/step down task is performed in the same manner described above for FIGS. 16A-16C, except that the obstacle or box 194' is positioned on a floor 196, rather than on the surface of the force measurement assembly 102. Advantageously, the placement of the box 194' on the floor 196, rather than on the surface of the force measurement assembly 102, enables a force measurement assembly 102 having a smaller footprint to be used for performing the motor task (i.e., because the force measurement assembly 102 is not required to accommodate the box 194' thereon). As shown in FIGS. 17A-17C, the box 194' is preferably placed adjacent to, and in close proximity to, a side of the force measurement assembly 102 so that a subject is able to easily to move back and forth between the force measurement assembly 102 and the box 194'. Moreover, as illustrated in FIGS. 17A-17C, the box 194' is preferably taller than the box 194 (i.e. it has a greater height), so that the step height (on and off the box 194') remains constant for the subject 108.

Figure 18A:
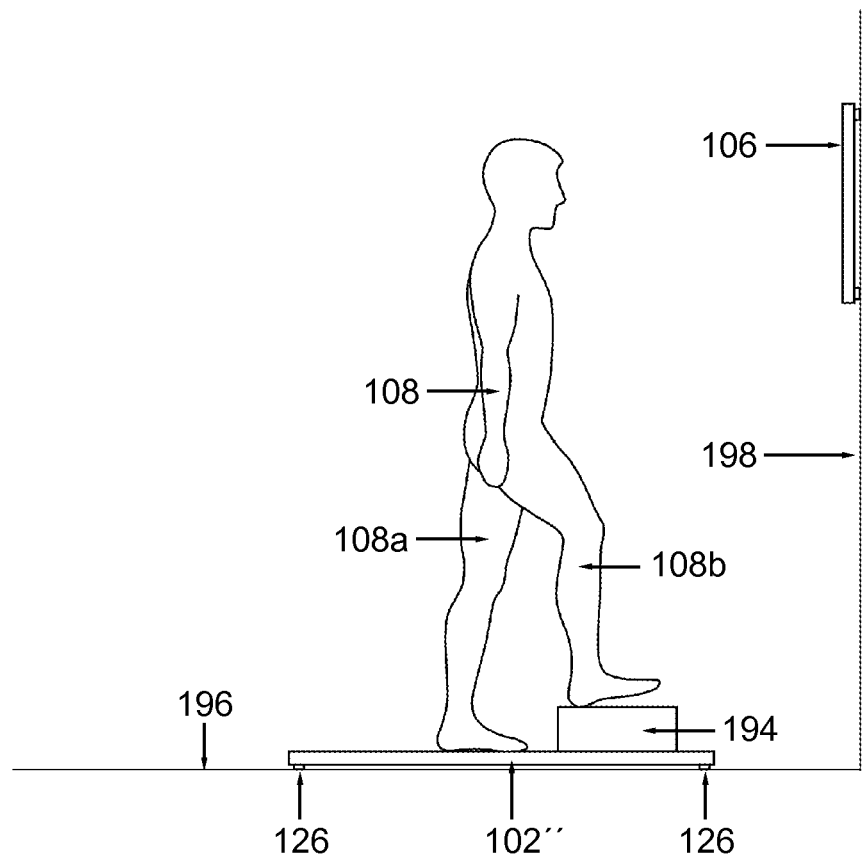
FIG. 18A diagrammatically illustrates a subject performing a first stage of an exemplary motor or muscular task on the surface of a third force measurement assembly, wherein the obstacle or box is disposed on the surface of the third force measurement assembly, according to an embodiment of the invention.
Figure 18B:
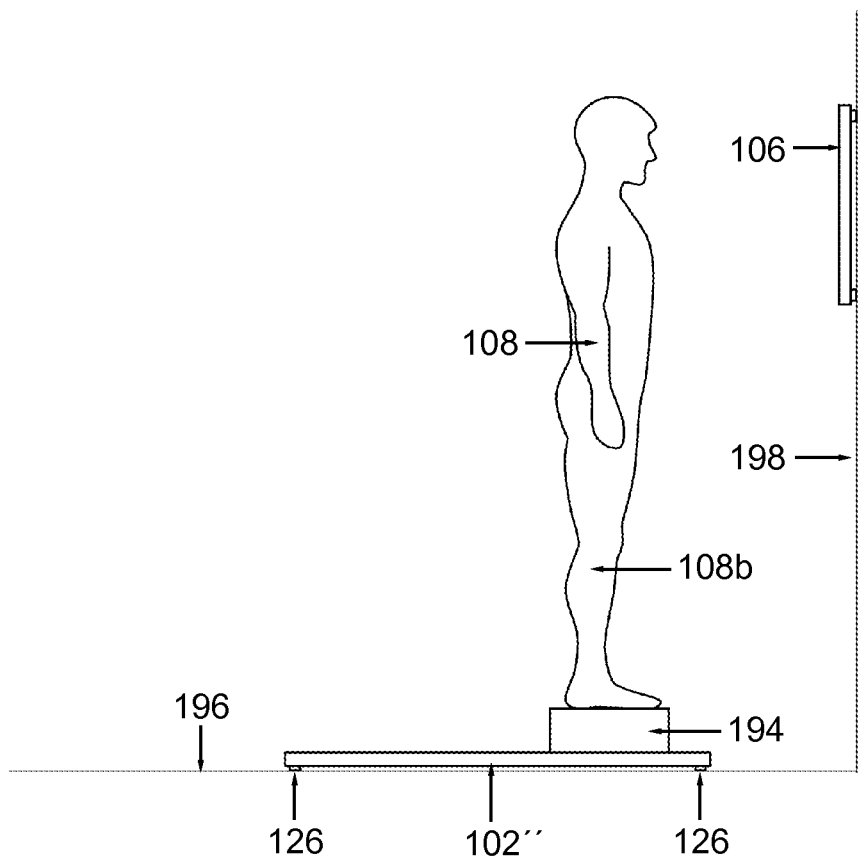
FIG. 18B diagrammatically illustrates a subject performing a second stage of an exemplary motor or muscular task on the surface of a third force measurement assembly, wherein the obstacle or box is disposed on the surface of the third force measurement assembly, according to an embodiment of the invention.
Figure 18C:
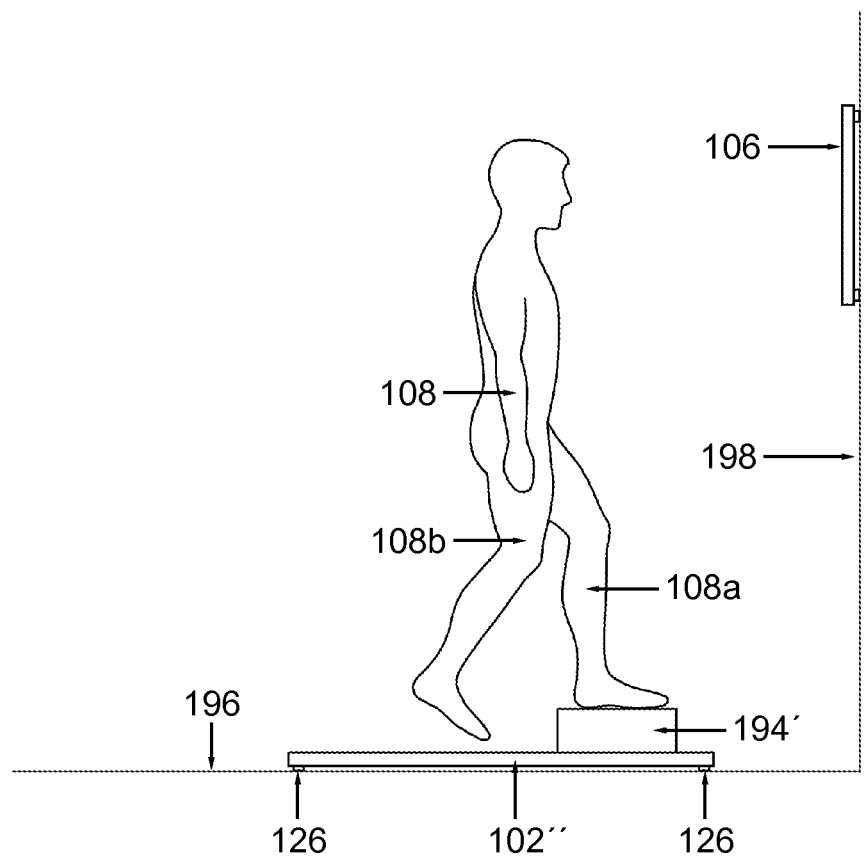
FIG. 18C diagrammatically illustrates a subject performing a third stage of an exemplary motor or muscular task on the surface of a third force measurement assembly, wherein the obstacle or box is disposed on the surface of the third force measurement assembly, according to an embodiment of the invention.

In FIGS. 18A-18C, the step up/step down protocol is performed in the same manner as that described above with regard to FIGS. 16A-16C. However, rather than using two force plate modules 102a, 102b as illustrated in FIGS. 16A-16C, only a single, longer force plate 102" is used. A longer force plate 102" is preferable when the box 194 is positioned thereon in order to ensure that the subject 108 has adequate space to perform the motor or muscular task.

In order to assess the performance of the subject 108 during the execution of the motor/muscular task (i.e., the step up/step down protocol), a plurality of performance parameters are computed by the data acquisition/data processing device 104 of the fall and/or concussion prediction system 100. For example, the mean movement time and the mean movement time difference are exemplary performances that may be computed by the data acquisition/data processing device 104. The mean movement time is the average amount of time required to complete the step up/step down protocol, and is expressed in seconds. The computation of the movement time begins with the initial center of pressure (COP) or center of gravity (COG) shift to the non-stepping (lagging or trailing) leg, and ends when both legs 108a, 108b are again repositioned on the surface of the force measurement assembly 102 (i.e., after the subject 108 has completed his or her backward movement onto the surface of the force measurement assembly 102). The values for each of the plurality of right leg trials are summed and divided by the total quantity of trials (e.g., two or three) to produce a right leg average, whereas the values for each of the plurality of left leg trials are summed and divided by the total quantity of trials (e.g., two or three) to produce a left leg average. The mean movement time difference is a comparison of the mean movement times over the left and right legs, expressed as a percentage. For example, the mean movement time difference can be computed as follows:

$$MMTD = \left[\frac{\bar{t}_L - \bar{t}_R}{\bar{t}_L + \bar{t}_R}\right] * 100\% \tag{10}$$

where:
MMTD: mean movement time difference, expressed as a percentage;
$\bar{t}_L$: average mean movement time of the left leg of the subject, expressed in seconds; and
$\bar{t}_R$: average mean movement time of the right leg of the subject, expressed in seconds.
If each leg accomplishes the movement in substantially a similar amount of time, then the difference would approximately equal zero (i.e., approximately 0%). Because the subject 108 is instructed to perform the task as quickly as possible, small values for the movement times are preferred, whereas high values for the movement times are not preferred. High values for the movement times, which are indicative of slow movement by the subject, may indicate that the subject has a disorder. During the performance of step up/step down protocol, the data acquisition/data processing device 104 may also compute a center of pressure (COP) tracing or center of gravity (COG) tracing for the subject 108 (i.e., the path of movement of the subject's COP or COG during the performance of the motor task).

Next, after the subject individually completes the cognitive task and the motor/muscular task, the subject then performs the cognitive task and the motor/muscular task simultaneously. During the simultaneous performance of the cognitive task and the motor/muscular task, performance parameters are computed for both of the two tasks by the data acquisition/data processing device 104. As shown in FIGS. 16A-16C, 17A-17C, and 18A-18C, the subject visual display device 106 is preferably positioned in front of the subject 108 (e.g., mounted on a wall 198 adjacent to the force measurement assembly 102, 102a/102b, 102") during the performance of the cognitive task and the motor/muscular task so that the subject 108 can easily performed both tasks together (e.g., the cognitive task would be displayed on the subject visual display device 106 while the subject 108 performs the motor task on the surface of the force measurement assembly 102). Advantageously, the subject visual display device 106 can also be used for giving the subject 108 instructions and/or cues at the onset of the motor task (e.g., to inform the subject 108 how to perform the task and/or to instruct the subject 108 when to begin the motor task).

The data acquisition/data processing device 104 is further configured to assess the probability that the subject will fall and/or predict whether or not the subject has sustained a concussion by using one or more of the performance parameters determined during the dual task protocol assessment. In particular, the data acquisition/data processing device 104 may assess the probability that the subject tested will fall by relating the subject's performance parameters during the dual task protocol to a fall probability classification. For example, a high value for the mean reaction time during the performance of the cognitive test (e.g., a mean reaction time of 30 seconds when the average healthy subject reaction time is 20 seconds) and/or a high value for the mean movement time during the performance of the motor or muscular task (e.g., a mean movement time of 4.5 seconds when the average healthy subject movement time is 3 seconds) is equated with an indication of a "High Fall Probability" classification of the subject. A relatively high value for the mean reaction time during the performance of the cognitive test (e.g., a mean reaction time of 25 seconds when the average healthy subject reaction time is 20 seconds) and/or a relatively high value for the mean movement time during the performance of the motor or muscular task (e.g., a mean movement time of 3.75 seconds when the average healthy subject movement time is 3 seconds) may be equated with an indication of a "Moderate Fall Probability" classification of the subject. In contrast, a low value for the mean reaction time during the performance of the cognitive test (e.g., a mean reaction time of 15 seconds when the average healthy subject reaction time is 20 seconds) and/or a low value for the mean movement time during the performance of the motor or muscular task (e.g., a mean movement time of 2.5 seconds when the average healthy subject movement time is 3 seconds) may be equated with an indication of a "Low Fall Probability" classification of the subject. At the conclusion of the testing, the appropriate classification of the subject is outputted to the subject visual display device 106 and/or the operator visual display device 156 so that the subject and/or the clinician can be informed of the subject's fall probability. The subject parameter values (i.e., reaction times and mean movement times) for the exemplary fall classifications listed above initially are established by collecting normative data from one or more groups of experimental test subjects. It is to be understood that these particular numerical values and/or ranges are presented for illustrative purposes only, and are in no way to be interpreted as limiting of the inventive scope.

In addition, the data acquisition/data processing device 104 may predict whether or not a subject has sustained a concussion by using one or more of the performance parameters determined during the dual task protocol assessment. For example, on day 1, prior to engaging in any athletic activities involving substantial contact with other players or another object (e.g., football or ice hockey), a first subject is tested several times using the fall and/or concussion prediction system 100, and has an average reaction time of 20 seconds for the cognitive task after being tested for three trials thereof (i.e., a baseline average reaction time), and a mean movement time of 3 seconds for the motor or muscular task after being tested for three trials thereof (i.e., a baseline mean movement time). Subsequently, on day 30, after playing football, and sustaining a severe impact to the head during a tackle, the same subject is again tested on the fall and/or concussion prediction system 100. However, on day 30, the first subject has an increased average reaction time of 30 seconds for the cognitive task after being tested for three trials thereof, and an increased mean movement time of 4.5 seconds for the motor or muscular task after being tested for three trials thereof. Based upon a comparison of the initial average reaction time value of 20 seconds to the subsequent average reaction time value of 30 seconds for the cognitive task, and/or a comparison of the initial mean movement time value of 3 seconds to the subsequent mean movement time value of 4.5 seconds for the motor or muscular task, the fall and/or concussion prediction system 100 determines that the subject has "Possibly Sustained a Concussion". As another example, on day 1, prior to engaging in any athletic activities involving substantial contact with other players or another object, a second subject is tested several times using the fall and/or concussion prediction system 100, and has an average reaction time of 22 seconds for the cognitive task after being tested for three trials thereof (i.e., a baseline average reaction time), and a mean movement time of 3.2 seconds for the motor or muscular task after being tested for three trials thereof (i.e., a baseline mean movement time). Subsequently, on day 45, after playing ice hockey, and sustaining a blow to the head from an opponent's hockey stick, the same subject is again tested on the fall and/or concussion prediction system 100. However, on day 45, the second subject has only a slightly increased average reaction time of 23 seconds for the cognitive task after being tested for three trials thereof, and only a slightly increased mean movement time of 3.3 seconds for the motor or muscular task after being tested for three trials thereof. Based upon a comparison of the initial average reaction time value of 22 seconds to the subsequent average reaction time value of 23 seconds for the cognitive task, and/or a comparison of the initial mean movement time value of 3.2 seconds to the subsequent mean movement time value of 3.3 seconds for the motor or muscular task, the fall and/or concussion prediction system 100 determines that the subject "Does Not Readily Appear to Have Sustained a Concussion". In some instances, the data acquisition/data processing device 104 may also conclude that it is "Indeterminable Whether or Not Subject Has Sustained a Concussion" (e.g., when scores achieved by the subject are too erratic). As described above for fall prediction, at the conclusion of the testing, the predicted concussion evaluation of the subject is outputted to the subject visual display device 106 and/or the operator visual display device 156 so that the subject and/or the clinician can be informed of whether or not the subject has most likely sustained a concussion.

As described above with regard to the interactive game, in one or more embodiments of the invention, the fall and/or concussion prediction system 100 is used to determine a subject's point of failure during the dual task protocol and/or determine the task during which the subject's failure occurs (e.g., a failure occurs during the cognitive task or the motor task). For example, during the performance of the second motor task, it may be determined that the failure occurs when the subject leans too much while performing the motor task. The subject's inability to perform the motor task without falling may be indicative of muscular disorder. Alternatively, the failure may occur during the performance of the cognitive task, which may be indicative of a cognitive disorder. Advantageously, once the subject's deficiency or deficiencies are identified, the appropriate corrective measures can be taken (e.g., if the failure occurred during the motor task, measures can be taken to treat the muscular disorder).

It is readily apparent that the embodiments of the fall and/or concussion prediction system 100 described above offer numerous advantages and benefits. The fall and/or concussion prediction system 100 discussed herein can be used to accurately assess a person's risk for falling and/or predict whether or not a person has sustained a concussion. Moreover, the fall and/or concussion prediction system 100 is capable of measuring the ability of a person to move his or her feet and shift his or her weight in response to visual cues. Furthermore, the fall and/or concussion prediction system 100 is capable of testing the dynamic balance of an individual by requiring the person to maintain his or her balance by shifting his or her weight in response to visual inputs that require mental processing.

Although the invention has been shown and described with respect to a certain embodiment or embodiments, it is apparent that this invention can be embodied in many different forms and that many other modifications and variations are possible without departing from the spirit and scope of this invention. For example, while a ball-type game is depicted in the illustrated embodiment, those of ordinary skill in the art will readily appreciate that the invention is not so limited. Rather, any game and/or protocol where playing and/or navigating gets more challenging over time can be used for the fall and/or concussion assessment system. As such, the claimed invention encompasses any such suitable game and/or protocol.

Moreover, it is to be understood that the functionality of the fall and/or concussion prediction system 100, which is described above in the context of an interactive game, is equally applicable in the context of a virtual reality scenario or an immersive graphic environment.

While exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A fall and/or concussion prediction system comprising, in combination:
    a measurement assembly configured to receive a subject, the measurement assembly including:
        a surface for receiving at least one portion of a body of a subject,
        at least one measurement device, the at least one measurement device configured to sense one or more measured quantities and output one or more signals that are generated based upon the subject's contact with the surface;
    a visual display device, the visual display device configured to display an interactive game, a virtual reality scenario, and/or an immersive graphic environment that is visible to the subject; and
    a data processing device operatively coupled to the at least one measurement device of the measurement assembly and the visual display device, the data processing device configured to receive the one or more signals that are generated based upon the subject's contact with the surface of the measurement assembly and to compute one or more numerical values using the one or more signals, the data processing device being configured to control the movement of at least one manipulatable element of the interactive game, the virtual reality scenario, and/or the immersive graphic environment displayed on the visual display device by using the one or more computed numerical values, the at least one manipulatable element being capable of affecting the motion of an object as it moves across the visual display device, the data processing device further configured to quantify a subject's performance while playing the interactive game, or while interacting with the virtual reality scenario and/or the immersive graphic environment, using one or more performance parameters, and to assess the probability that the subject will fall and/or predict whether or not the subject has sustained a concussion by using the one or more performance parameters.

2. The fall and/or concussion prediction system according to claim 1, wherein the one or more performance parameters are indicative of the subject's balance, visual acuity, and reaction time.

3. The fall and/or concussion prediction system according to claim 1, wherein a difficulty level of the interactive game, the virtual reality scenario, and/or the immersive graphic environment progressively increases over time.

4. The fall and/or concussion prediction system according to claim 1, wherein the object moves increasingly faster across the visual display device as the interactive game, the virtual reality scenario, and/or the immersive graphic environment progresses over time.

5. The fall and/or concussion prediction system according to claim 1, wherein the at least one manipulatable element comprises a first manipulatable element and a second manipulatable element, the first manipulatable element and the second manipulatable element each being capable of affecting the motion of the object as it moves across the visual display device.

6. The fall and/or concussion prediction system according to claim 5, wherein the first manipulatable element and the second manipulatable element are disposed on generally opposite sides of the visual display device.

7. The fall and/or concussion prediction system according to claim 5, wherein the measurement assembly comprises a force measurement assembly, and wherein the one or more numerical values computed using the one or more signals comprise x and y coordinates specifying the center of pressure of a force vector applied by the subject on the force measurement assembly, wherein a value of the x coordinate of the center of pressure determines which one of the first manipulatable element and the second manipulatable element is active, and a value of the y coordinate of the center of pressure determines a translational movement of an active one of the first manipulatable element and the second manipulatable element.

8. The fall and/or concussion prediction system according to claim 1, wherein the measurement assembly comprises one of a force measurement assembly, a pressure measurement assembly, and a contact or timing measurement assembly; and wherein the at least one measurement device comprises one of a force transducer, a pressure transducer, and a contact or timing switch.

9. A fall and/or concussion prediction system comprising, in combination:

a measurement assembly configured to receive a subject, the measurement assembly including:
  a first measurement surface for receiving a first portion of a body of a subject,
  a second measurement surface for receiving a second portion of a body of a subject,
  at least one first measurement device, the at least one first measurement device configured to sense one or more measured quantities and output one or more first signals that are generated based upon the subject's contact with the first measurement surface, and
  at least one second measurement device, the at least one second measurement device configured to sense one or more measured quantities and output one or more second signals that are generated based upon the subject's contact with the second measurement surface;

a visual display device, the visual display device configured to display an interactive game, a virtual reality scenario, and/or an immersive graphic environment that is visible to the subject; and a data processing device operatively coupled to the first and second measurement devices of the measurement assembly and the visual display device, the data processing device configured to receive the one or more first signals that are generated based upon the subject's contact with the first measurement surface and compute one or more first numerical values using the one or more first signals, the data processing device being configured to receive the one or more second signals that are generated based upon the subject's contact with the second measurement surface and compute one or more second numerical values using the one or more second signals, the data processing device further configured to control the movement of a first manipulatable element of the interactive game, the virtual reality scenario, and/or the immersive graphic environment displayed on the visual display device by using the one or more first numerical values, and to control the movement of a second manipulatable element of the interactive game, the virtual reality scenario, and/or the immersive graphic environment displayed on the visual display device by using the one or more second numerical values, the data processing device additionally configured to quantify a subject's performance while playing the interactive game, or while interacting with the virtual reality scenario and/or the immersive graphic environment, using one or more performance parameters, and to assess the probability that the subject will fall and/or predict whether or not the subject has sustained a concussion by using the one or more performance parameters.

10. The fall and/or concussion prediction system according to claim 9, wherein the one or more performance parameters are indicative of the subject's balance, visual acuity, and reaction time.

11. The fall and/or concussion prediction system according to claim 9, wherein the first manipulatable element and the second manipulatable element are each capable of affecting the motion of an object as it moves across the visual display device.

12. The fall and/or concussion prediction system according to claim 11, wherein the object moves increasingly faster across the visual display device as the interactive game, the virtual reality scenario, and/or the immersive graphic environment progresses over time.

13. The fall and/or concussion prediction system according to claim 9, wherein the first manipulatable element and the second manipulatable element are disposed on generally opposite sides of the visual display device.

14. The fall and/or concussion prediction system according to claim 9, wherein the measurement assembly comprises a force measurement assembly, and wherein the one or more first numerical values computed using the one or more first signals include a magnitude of the force applied to the first measurement surface by the subject, the one or more second numerical values computed using the one or more second signals include a magnitude of the force applied to the second measurement surface by the subject, and wherein a comparison between the magnitudes of the forces applied to the first and second measurement surfaces by the subject determines which one of the first manipulatable element and the second manipulatable element is active.

15. The fall and/or concussion prediction system according to claim 9, wherein the measurement assembly comprises a force measurement assembly, and wherein the one or more first numerical values computed using the one or more first signals further include a coordinate specifying a location of a first force vector applied by the subject on the first measurement surface, the one or more second numerical values computed using the one or more second signals further include a coordinate specifying a location of a second force vector applied by the subject on the second measurement surface, wherein a value of the coordinate of the first force vector determines a translational movement of the first manipulatable element and a value of the coordinate of the second force vector determines a translational movement of the second manipulatable element.

16. The fall and/or concussion prediction system according to claim 9, wherein the measurement assembly comprises one of a force measurement assembly, a pressure measurement assembly, and a contact or timing measurement assembly; and wherein the at least one first measurement device and the at least one second measurement device each comprise one of a force transducer, a pressure transducer, and a contact or timing switch.

17. A method for fall and/or concussion prediction, the method comprising the steps of:

providing a measurement assembly configured to receive a subject thereon, the measurement assembly including:
  a surface for receiving at least one portion of a body of a subject, and
  at least one measurement device, the at least one measurement device configured to sense one or more measured quantities and output one or more signals that are generated based upon the subject's contact with the surface;

providing a visual display device configured to display a scene of a first task that is visible to the subject;

providing a data processing device operatively coupled to the at least one measurement device of the measurement assembly and the visual display device;

positioning the subject on the measurement assembly;

displaying the scene of the first task on the visual display device so that it is visible to the subject;

instructing the subject to perform a first task, which relates to the scene on the visual display device, and a second task, which comprises one or more movements on the surface of the measurement assembly;

sensing, by utilizing the at least one measurement device, one or more measured quantities and outputting one or more signals that are generated based upon the subject's contact with the surface of the measurement assembly;

receiving, at the data processing device, the one or more signals that are generated based upon the subject's contact with the surface of the measurement assembly;

computing, by using the data processing device, one or more numerical values from the one or more signals outputted by the at least one measurement device;

quantitatively determining, by using the data processing device, a subject's performance during the first and second tasks, the assessment of the subject's performance of the second task being based at least partially upon the one or more numerical values, the subject's performance of the first task being quantitatively expressed in terms of one or more first performance values and the subject's performance of the second task being quantitatively expressed in terms of one or more second performance values; and determining the probability that the subject will fall and/or predicting whether or not the subject has sustained a concussion by using at least one of the one or more first and second performance values.

18. The method according to claim 17, wherein the first task comprises a cognitive task and the second task comprises a motor or muscular task.

19. The method according to claim 18, wherein the one or more first performance parameters for assessing the subject's performance of the cognitive task comprise one or more of the following: (i) a reaction time of the subject and (ii) an accuracy value for the subject in performing one or more exercises of the cognitive task.

20. The method according to claim 18, wherein the one or more second performance parameters for assessing the subject's performance of the motor or muscular task comprise one or more of the following: (i) a reaction time of the subject, (ii) a mean movement time of the subject, (iii) a mean movement time difference of the subject, (iv) a sway range of the center of pressure of a force vector applied by the subject on the measurement assembly, (v) a velocity of the center of pressure of a force vector applied by the subject on the measurement assembly, (vi) a sway range of the center of gravity of the subject, and (vii) a velocity of the center of gravity of the subject.

21. The method according to claim 18, wherein the first cognitive task comprises one or more of the following: (i) answering a series of multiple choice questions, (ii) identifying a particular letter or letters that have a logical relationship to a predetermined letter or pattern of letters, (iii) identifying a particular number or numbers that have a logical relationship to a predetermined number or pattern of numbers, and (iv) identifying a particular symbol or symbols that have a logical relationship to a predetermined symbol or pattern of symbols.

22. The method according to claim 18, wherein the second motor or muscular task comprises one or more of the following: (i) walking or running a predetermined distance, (ii) maintaining a static position, (iii) maintaining balance on a moving surface, (iv) balancing one or more objects, (v) moving from a standing position to a seated position, (vi) moving from a seated position to a standing position, (vii) stepping up and over a predetermined obstruction, and (viii) stepping up and down on and off a predetermined obstruction.

23. The method according to claim 17, wherein the measurement assembly comprises one of a force measurement assembly, a pressure measurement assembly, and a contact or timing measurement assembly; and wherein the at least one measurement device comprises one of a force transducer, a pressure transducer, and a contact or timing switch.

24. The method according to claim 17, further comprising the step of:

delivering an auditory input to the subject during the first task.

* * * * *